United States Patent [19]

Hamaguri et al.

[11] Patent Number: 4,714,341

[45] Date of Patent: Dec. 22, 1987

[54] MULTI-WAVELENGTH OXIMETER HAVING A MEANS FOR DISREGARDING A POOR SIGNAL

[75] Inventors: Kenji Hamaguri, Minamikawachi; Takao Sakai, Habikino, both of Japan

[73] Assignee: Minolta Camera Kabushiki Kaisha, Osaka, Japan

[21] Appl. No.: 704,772

[22] Filed: Feb. 21, 1985

[30] Foreign Application Priority Data

Feb. 23, 1984 [JP] Japan .................................. 59-33952
Mar. 12, 1984 [JP] Japan .................................. 59-47769

[51] Int. Cl.$^4$ ............................................. G01N 33/16
[52] U.S. Cl. ....................................... 356/41; 128/633; 364/416
[58] Field of Search ................. 356/41, 320, 406, 407, 356/414, 416, 417, 419; 128/633, 664, 665, 666

[56] References Cited

U.S. PATENT DOCUMENTS

| | | | |
|---|---|---|---|
| 3,638,640 | 2/1972 | Shaw | 356/41 |
| 3,998,550 | 12/1976 | Konishi et al. | 356/41 |
| 4,086,915 | 5/1978 | Kofsky et al. | 356/41 |
| 4,114,604 | 10/1976 | Shaw et al. | 356/41 |
| 4,167,331 | 9/1979 | Nielsen | 356/41 |
| 4,407,290 | 10/1983 | Wilber | 356/41 |
| 4,453,218 | 6/1984 | Sperinde et al. | 364/416 |
| 4,586,513 | 5/1985 | Hamaguri | 128/663 |

FOREIGN PATENT DOCUMENTS 50-128387  10/1975  Japan .

OTHER PUBLICATIONS

Photoelectric Determination of Arterial Oxygen Saturation in Man.
New Contributions to the Optics of Intensely Light-Scattering Materials, Part I, by Paul Kubelka.

*Primary Examiner*—R. A. Rosenberger
*Attorney, Agent, or Firm*—Price, Gess & Ubell

[57] ABSTRACT

An oximeter for measuring oxygen saturation in arterial blood includes a light source for projecting light to a body member to be measured, a light responsive circuit for receiving the light which has transmitted through said body member and for generating at least first, second and third signals at three different wavelengths, and a calculator for calculating at least first $SaO_2$ data using first and second signals and second $SaO_2$ data using first and third signals. It is detected whether or not a difference between the first and second $SaO_2$ data is within a predetermined level. When the difference is within the predetermined level, it is assumed that the first and/or second $SaO_2$ data are valid, but if not, they are assumed as invalid.

12 Claims, 20 Drawing Figures

Fig. 10
Fig. 11
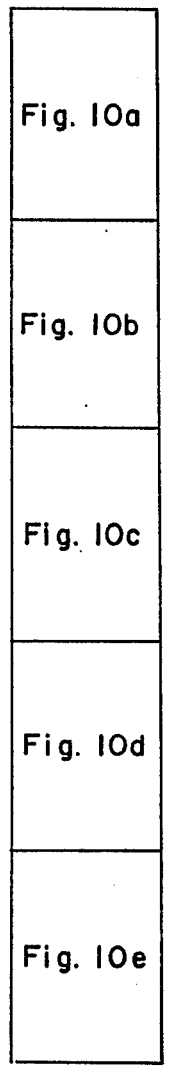
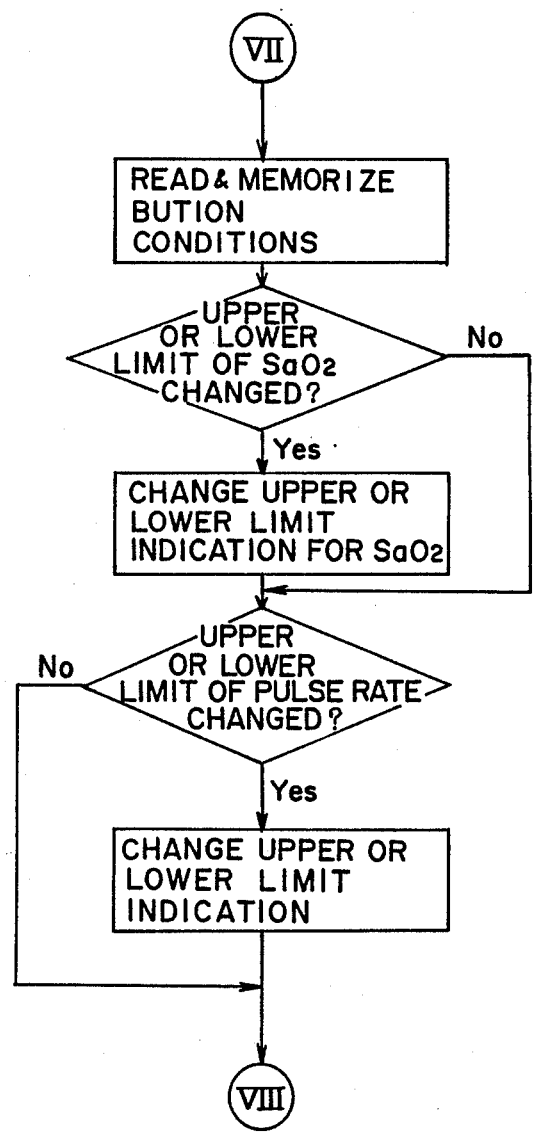

MULTI-WAVELENGTH OXIMETER HAVING A MEANS FOR DISREGARDING A POOR SIGNAL

BACKGROUND OF THE INVENTION

1. Field of the Invention

The present invention relates to an oximeter and, more particularly, to an apparatus for measuring the degree of oxygen saturation of arterial blood (hereinafter also referred to as $SaO_2$) a non-invasive manner.

2. Description of the Prior Art

The oximeter of non-invasive type generally has a source of a light from which a light is directed to a body member of the subject, such as a finger or ear lobe. The light passes through the body member and is then detected by the detector. The amount of light absorbed by the body member as light is transmitted through it is a function of the attenuation which is dependent on the amount of oxygenated hemoglobin in the arterial blood in the body member. Accordingly, by measuring the transmitted light, oxygen saturation ($SaO_2$) in the arterial blood can be determined.

According to the prior art oximeter of the above described type, the active motion of the body member, such as a movement of the body member or an irregular pulse of blood pressure causes an undesirable change in the light amount measured by the detector, thus resulting in undesirable noise signal in the detected signal. Since it is impossible to stop the active motion of the body member, a means for detecting the active motion is provided. When the detecting means detects the active motion, the measured result is ignored. Here, the problem is to provide such a detecting means which has a high accuracy in detecting the active motion in the body member.

According to a first prior art oximeter, the active motion is detected by the detection of a sudden and great change in the amplitude of the pulse signal. In this case, the active motion with a sudden change can be detected, but the active motion that changes gradually and incessantly can not be detected.

According to a second prior art oximeter, the active motion is detected by the detection of a difference in the step-up time, or step-down time, between the pulse signal under active motion and pulse signal under a steady condition. However, because of wide variations between patients in such a step-up time or step-down time, and even in the same patient due to the environmental change, the accuracy of the detected result is very poor.

According to a third prior art oximeter, the active motion is detected by the detection of change in the pulse rate. This oximeter, however, can not detect the active motion when the active motion occurs periodically.

An improved oximeter, which is invented by one of the present invention, Kenji HAMAGURI, and is assigned to the same assignee, is disclosed in Japanese Patent Laid-open Publication (Tokkaisho) No. 55-120858. According to this publication, the light passed through the body member is detected at three different wavelengths. Using the detected amount of light Ea1, Ea2 and Ea3 at three different wavelengths, the amount of absorption Eb1, Eb2 and Eb3 by the blood in the body member is calculated for each of the three wavelengths. Then, differences Ec1 and Ec2 are obtained through the calculations:

$$Ec1 = Eb1 - Eb3$$

and $$Ec2 = Eb2 - Eb3.$$

Then, using the obtained differences Ec1 and Ec2, the degree of oxygen saturation of arterial blood ($SaO_2$) is obtained.

Even in this improved oximeter, since the oxygen saturation ($SaO_2$) is calculated using the signal which has been already influenced by the active motion of the body, the influence of the active motion can not be completely removed from the result obtained from the improved oximeter. In the case where the action motion is great, the obtained result will be very poor in reliability.

Also, according to the prior art of noninvasive type, a digital display device and/or an analog current meter are employed for the indication of oxygen saturation ($SaO_2$) and pulse rate in the instantaneous values or in the averaged values. By the continuous watch on the patient's oxygen saturation using the oximeter of noninvasive type, the sudden condition change of the patient can be catched easily. However, with the digital display device or analog current meter itself, it is difficult to know the gradual condition change of the patient.

Furthermore, according to the prior art oximeter, the indication through the digital display device and/or the analog current meter is effected after a certain period of time, but when it is detected that the measured result does not have a sufficient accuracy, the indication is skipped. When the skipping takes place for a number of times frequently, the indication on the display is effected irregularly.

Accordingly, because of the disadvantages mentioned above, it has been difficult to obtain accurate and trustworthy results from the oximeter of the prior art.

SUMMARY OF THE INVENTION

The present invention has been developed with a view to substantially solving the above described disadvantages and has for its essential object to provide an improved oximeter of non-invasive type which can provide a degree of oxygen saturation of arterial blood ($SaO_2$) with a high accuracy.

It is also an essential object of the present invention to provide an oximeter of the above described type which can present the obtained data in various fashions to utilize the data in every possible way.

In accomplishing these and other objects, an oximeter according to the present invention comprises a light source for projecting light to a body member to be measured, a light responsive circuit for receiving the light which has transmitted through said body member and for generating at least first, second and third signals at three different wavelengths, and a calculator for calculating at least a first $SaO_2$ data using first and second signals and second a $SaO_2$ data using first and third signals. Then, it is detected whether or not a difference between the first and second $SaO_2$ data is within a predetermined level. When the difference is within the predetermined level, it is assumed that the first and/or second $SaO_2$ data are valid, but if not, they are assumed as invalid.

BRIEF DESCRIPTION OF THE DRAWINGS

These and other objects and features of the present invention will become apparent from the following description taken in conjunction with preferred embodiments thereof with reference to the accompanying drawings, throughout where like parts are designated by like reference numerals, and in which:

FIG. 1b is a graph showing waveforms obtained from major points in the circuit of FIG. 1a;

FIG. 2 is a diagrammatic view of a light source used in the circuit of FIG. 1a;

FIG. 11 is a flow chart showing an operation for setting upper and lower limits for $SaO_2(2)$ and pulse rate;

THEORY OF $SaO_2$ MEASURING ACCORDING TO THE INVENTION

Figure 1A:
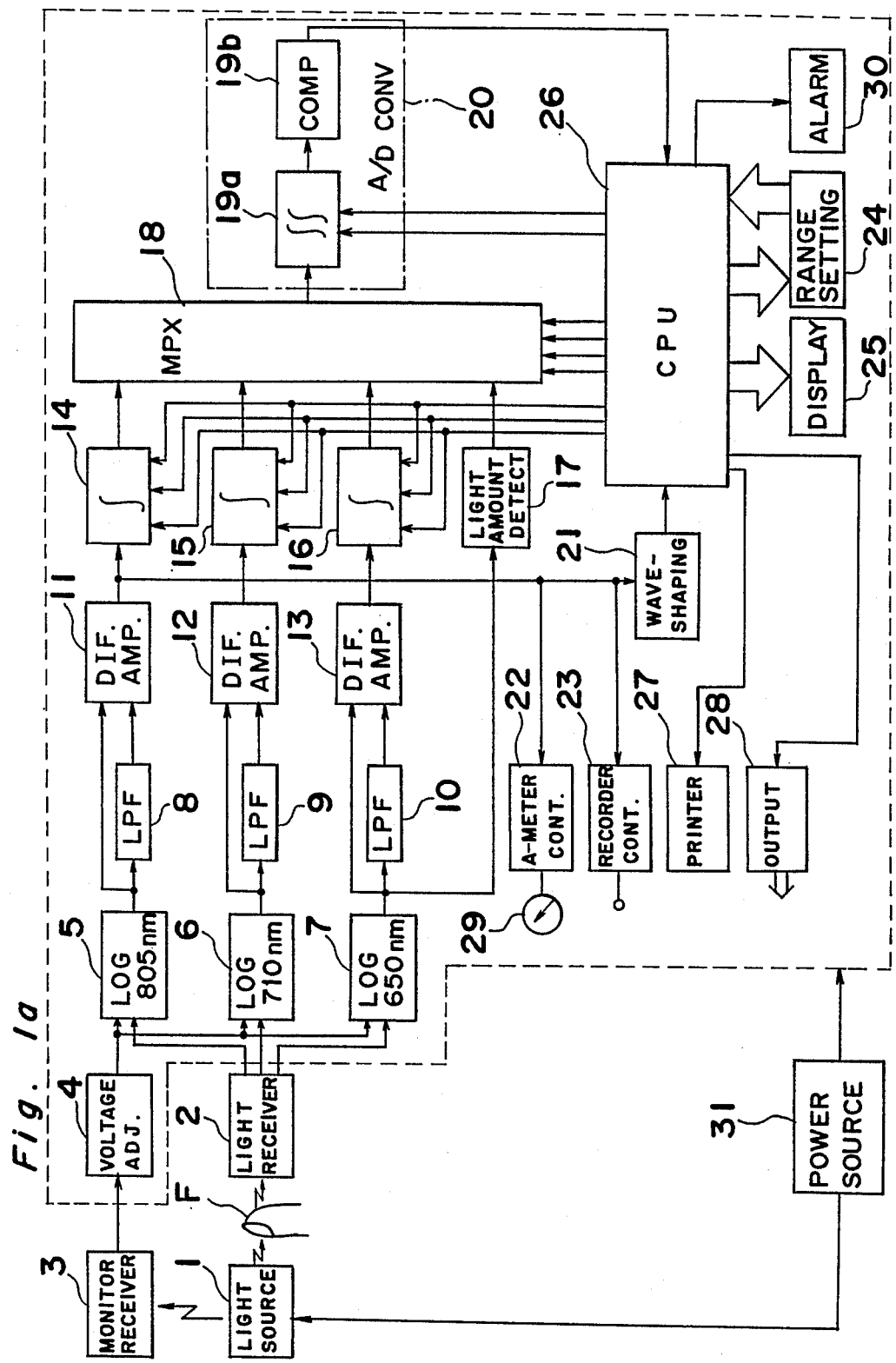
FIG. 1a is a block diagram of an oximeter according to a first embodiment of the present invention.

Before the description proceeds to the preferred embodiments, the theory of measuring the degree of oxygen saturation of arterial blood ($SaO_2$) is described.

When light transmits through the body member, it is absorbed and scattered by blood, muscle, and other members constituting the body member. Thus the transmitted light is attenuated. Since the arterial blood is pulsating, its volume at a place where the light transmits changes periodically. Thus, the degree of attenuation of the transmitted light also changes periodically. The intensity Iw of the light, having a wavelength w, transmitted through the body member can be given as follows:

$$Iw = Iow \times Ftw \times Fvw \times f(Qw)e^{-g(Qw)(d+\Delta d)},$$

wherein Iow is an intensity of light directed to the body member; Ftw is a transmittance of a bloodless body member; Fvw is a transmittance of a body member with venous blood; Qw is an absorption coefficient of light having the wavelength w with arterial blood; f(Qw) and g(Qw) are functions with a variable Qw; $d + \Delta d$ is a thickness of the body member; and $\Delta d$ is the change in the thickness of the body member that takes place periodically.

A DC component Yw in the logarithmically compressed values of Iw can be given:

$$Yw = -g(Qw)\Delta d.$$

Since g(Qw) is approximately proportional to the square root of Qw, the above equation may be written:

$$Yw^2 = kwQw(\Delta d)^2,$$

wherein kw is a constant determined dependently on the wavelength w. The absorption coefficient Qw can be given:

$$Qw = CHbo_2 \times EwHbo_2 + CHb + EwHb$$
$$= Ct[S(EwHbo_2 - EHb) + EwHb],$$

in which $$Ct = CHbo_2 + CHb$$

and $$S = CHbo_2/Ct = CHbo_2/(CHbo_2 + CHb),$$

and wherein $CHbo_2$ and $CHb$ are the amounts of oxyhemoglobin and deoxyhemoglobin, respectively, in a unit volume; and $EwHbo_2$ and $EwHb$ are absorption coefficients of the light with the wavelength w in oxyhemoglobin and deoxyhemoglobin, respectively. Accordingly, $Yw^2$ can be given as follows:

$$Yw^2 = kwCt[S(EwHbo_2 - EwHb) + EwHb](\Delta d)^2.$$

By obtaining two different DC components Yw1 and Yw2 at two different wavelengths w1 and w2, it is possible to calculate the ratio S in a manner described below.

Since $$(Yw1)^2 = kw1Ct[S(Ew1Hbo_2 - Ew1Hb) + Ew1Hb](\Delta d)^2$$

and $$(Yw2)^2 = kw2Ct[S(Ew2Hbo_2 - Ew2Hb) + Ew2Hb](\Delta d)^2,$$

we obtain $$S = \frac{Ew2Hb \times \frac{Yw1^2}{kw1} - Ew1Hb \times \frac{Yw2^2}{kw2}}{(Ew2Hbo_2 - Ew2Hb) \times \frac{Yw1^2}{kw1} - (Ew1Hbo_2 - Ew1Hb) \times \frac{Yw2^2}{kw2}}$$

By selecting a certain light having a wavelength w1 which satisfies an equation:

$$Ew1Hbo_2 = Ew1Hb,$$

the above equation can be simplified as:

$$S = \frac{kw1}{kw2} \times \frac{Ew1Hb}{Ew2Hbo_2 - Ew2Hb} \times \left(\frac{Yw2}{Yw1}\right)^2 -$$

-continued $$\frac{Ew2Hb}{Ew2Hbo_2 - Ew2Hb}.$$

Since the degree of oxygen saturation of arterial blood (SaO$_2$) can be defined as $$SaO_2 = S \times 100(\%),$$

the above equation may be written as:

$$SaO_2 = A \times \left(\frac{Yw2}{Yw1}\right)^2 + B,$$

wherein A and B are amounts which can be obtained from the optical characteristics of the blood. When A and B are fixed, SaO$_2$ is in relation to Yw2/Yw1. Therefore, a term "SaO$_2$ data" represents not only A×(Yw2/Yw1)$^2$+B, but also (Yw2/Yw1)$^2$ and Yw2/Yw1.

DESCRIPTION OF THE PREFERRED EMBODIMENTS

Figure 1B:
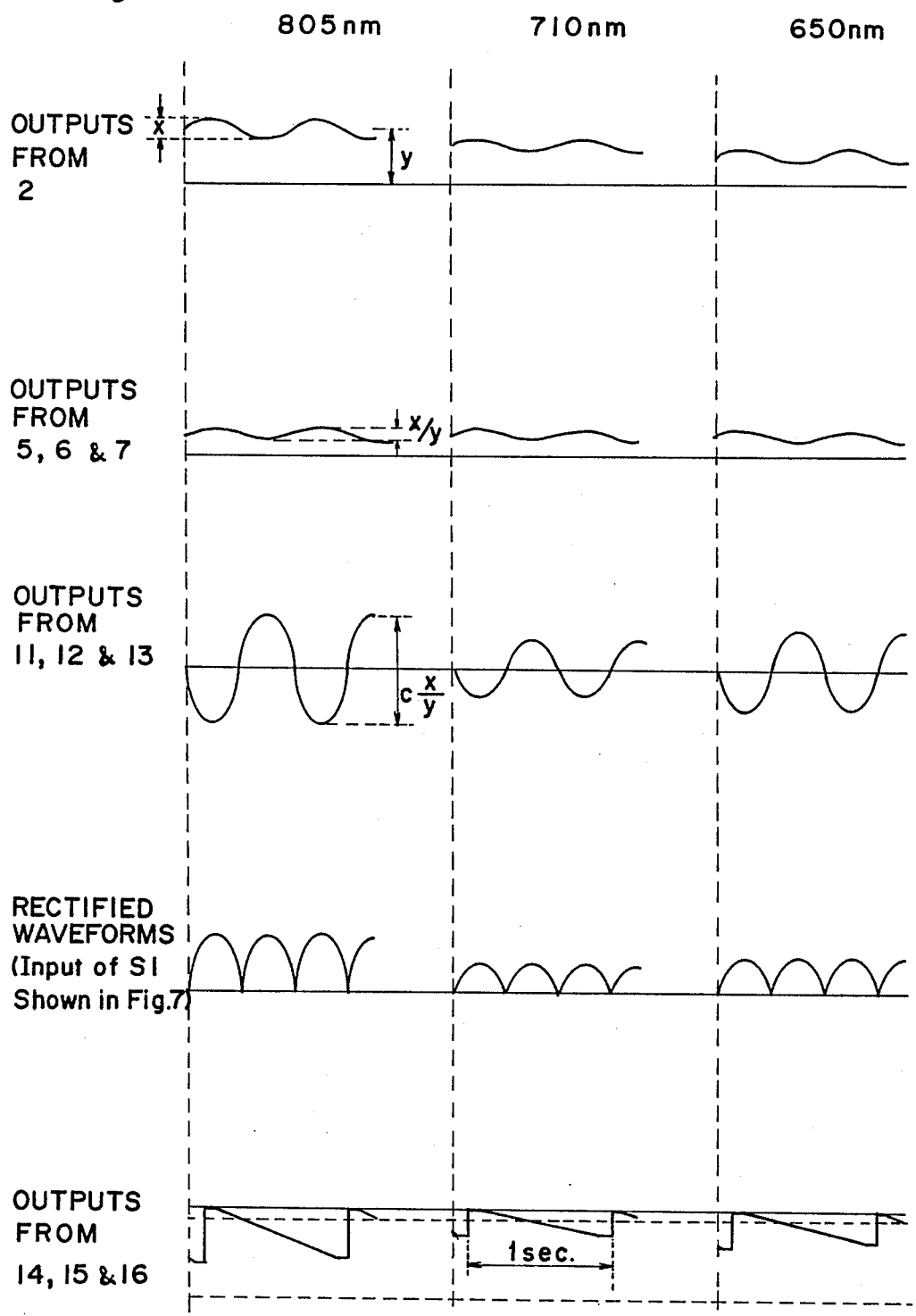

Referring to FIG. 1a, a body member F, such as a finger, is steadily held between a light source 1, such as a halogen lamp, and a light receiver 2. Light receiver 2 is sensitive to light at three different wavelengths, which are, e.g., 805, 710 and 650 nanometers. It is to be noted that these figures are given merely as an example, and, therefore, any other figures can be used. Thus, light receiver 2 generates three different signals representing the intensity of light at three different wavelengths. The generated signals are applied to logarithmic circuits 5, 6 and 7, respectively. According to a preferred embodiment, light receiver 2 includes three photoelectric cells 36, 37 and 38, shown in FIG. 3, which are coupled to I/V (current-to-voltage) converters 39, 40 and 41, respectively. Thus, converters 39, 40 and 41 generate voltage signals representing the light intensity at wavelengths 805, 710 and 650 nanometers, respectively. These signals produced from I/V converters 39, 40 and 41 are substantially equal to the signals produced from light receiver 2, and are applied to logarithmic amplifiers 42, 43 and 44 provided in logarithmic circuits 5, 6 and 7, respectively. The signals produced from light receiver 2 are composite signal having both AC and DC components, as shown in FIG. 1b, first row. As indicated therein, each signal is carried on a different DC level y and has a different amplitude x of fluctuation. The fluctuation is caused by the heart pulsation of the body.

The difference in the DC level is caused by the difference of the light intensity at three different wavelengths. Therefore, it is necessary to compensate the voltage signals obtained from I/V converters 39, 40 and 41 in such a way that the signals are obtained in the same condition, so that three signals have the same DC level. To this end, the light from light source 1 is also applied to a monitor receiver 3 which monitors the intensity of the light at three different wavelengths, which are the same as those mentioned above.

Figure 3:
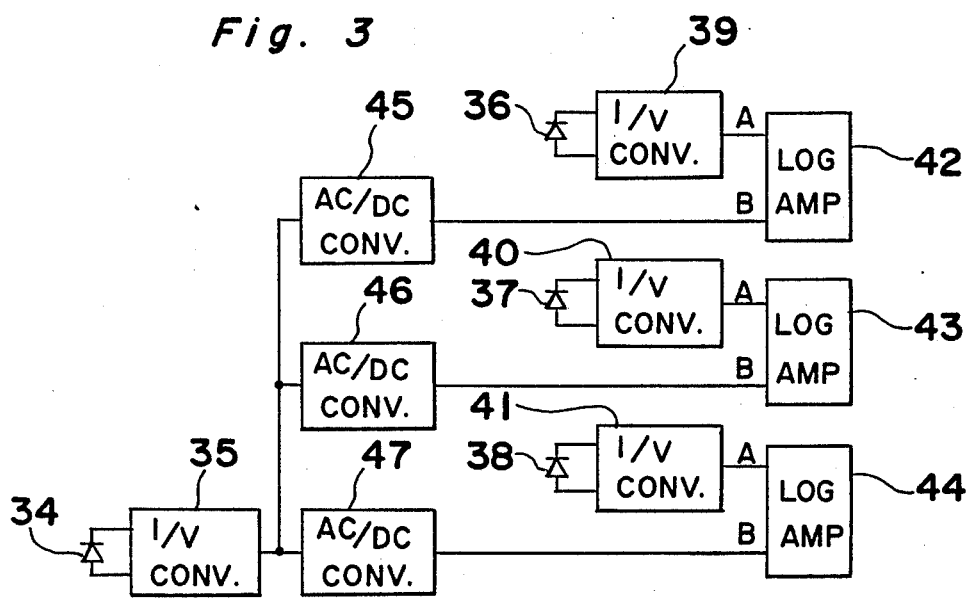
FIG. 3 is a block diagram showing a detail of circuits from photoelectric cells to logarithmic amplifiers.

According to the preferred embodiment, as shown in FIG. 3, monitor receiver 3 includes one photoelectric cell 34, which is coupled to an I/V converter and further to three AD/DC converters 45, 46 and 47. As will be described in detail later, AC/DC converters 45, 46 and 47 generate voltage signals indicating the intensity of direct light from light source 1 at three different wavelengths. The signals from AD/DC converters 45, 46 and 47 are applied to logarithmic amplifiers 42, 43 and 44 to change the gain therein. Thus, the voltage signals obtained from I/V converters 39, 40 and 41 can be evaluated under the same condition such that the light intensity at three different wavelengths from light source 1 are the same. Accordingly, the outputs from logarithmic amplifiers 42, 43 and 44, that is, outputs from logarithmic circuits 5, 6 and 7 are carried on the same DC level, and the signal on the DC level is identical to x/y, as indicated in FIG. 1b, second row.

Referring back to FIG. 1a, the output of logarithmic circuit 5 is applied to a low pass filter 8 for passing unwanted low frequency, such as 3 Hz, noise to a differential amplifier 11. Differential amplifier 11 also receives the signal directly from logarithmic circuit 5. Accordingly, differential amplifier 11 generates only the AC component amplified by a certain gain, as indicated in FIG. 1b, third row. The output of differential amplifier 11 is connected to a full-wave rectifier 14 which rectifies the output signal from differential amplifier 11, as indicated in FIG. 1b, fourth row, and integrates the rectified signal for a predetermined period of time, such as 1 second, repeatedly. The output of full-wave rectifier 14, such as shown in FIG. 1b, last row, is applied to a multiplexer 18.

In a similar manner, the output of logarithmic circuit 6 is connected through a low pass filter 9, a differential amplifier 12 and an full-wave rectifier 15 to multiplexer 18. Also, the output of logarithmic circuit 7 is connected through a low pass filter 10, a differential amplifier 13 and an full-wave rectifier 16 to multiplexer 18. The output of logarithmic circuit 7 is further connected to a light amount detector 17 which carries out a certain calculation to detect the amount of light received by light receiver 2. The output of light amount detector 17 is applied to multiplexer 18 for use in detecting whether or not the amount light received by receiver 2 is above a predetermined level sufficient for the SaO$_2$ detection.

Multiplexer 18 selects one of the outputs from circuits 14, 15, 16 and 17 and sequentially transmits the selected output to an A/D (analog-to-digital) converter 20, which is defined by a double integrator 19a and a comparator 19b. Thus, the analog signal obtained from multiplexer 18 is changed to a digital signal, which is applied to a CPU (central processing unit) 26. CPU 26 also receives the signal from differential amplifier 11 through a wave-shaping circuit 21 so as to count the pulse rate of the patient.

The output of differential amplifier 11 is also applied to an ampere meter control 22 which changes the received signal to a fashion capable of driving an ampere meter 29, and to a recorder control 23 which changes the received signal to a fashion capable of operating a recorder (not shown).

CPU 26 is coupled with various devices, such as: an alarm device 30 for producing an alarm sound when an obtained signal fails to fall within a selected range; a range setting device 24 which has a number of switches for setting upper and lower limits of the range and switches for controlling the generation of alarm sound; a display device 25 for displaying various data, such as measured SaO$_2$ and pulse rate; printer 27 for making a hard copy of the information shown on display device 25; and a digital output device 28 capable of being connected to an external device, such as a printer (not shown). CPU 26 also produces various control signals for controlling the sequence of operation of the circuits 14, 15, 16, 18 and 20, and devices 24, 25 and 30. It also carries out various control steps, which will be described later in connection with FIGS. 10a–10e, for obtaining SaO$_2$ and pulse rate.

According to the first embodiment, the oximeter further includes a power source 31 for supplying power to the circuits and devices shown in FIG. 1a.

According to the preferred embodiment, the light source 1, shown as a halogen lamp, emits light which is directed partially to a photoelectric cell provided in monitor receiver 3, and partially directed through an optical path defined, e.g., by an optical fiber (not shown) to a light measuring portion. At the light measuring portion, the light is separated into a spectrum for obtaining the three different wavelength lights, which are directed to three different photoelectric cells 36, 37 and 38. Each of the photoelectric cells 36, 37 and 38 and the one provided in monitor receiver 3 produces a current signal which is in relation to the intensity of received light. The current signal produced from monitor receiver 3 is converted to a voltage signal in a voltage adjuster 4, and the voltage signal is applied to each of logarithmic circuits 5, 6 and 7.

Logarithmic circuit 5 receives the voltage signal from voltage adjuster 4 and also the voltage signal from light receiver 2 and produces a logarithmically compressed voltage signal carrying information about a particular wavelength light (such as light having a wavelength of 805 nanometers). Similarly logarithmic circuit 6 receives the voltage signal from voltage adjuster 4 and also the voltage signal from light receiver 2 and produces a logarithmically compressed voltage signal carrying information about a particular wavelength light (such as light having a wavelength of 710 nanometers). Furthermore, logarithmic circuit 7 receives the voltage signal from voltage adjuster 4 and also the voltage signal from light receiver 2 and produces a logarithmically compressed voltage signal carrying information about a particular wavelength light (such as light having a wavelength of 650 nonometers).

Each of the logarithmic circuits 5, 6 and 7 includes, as will be described later, a correction circuit which will eliminate the noise signal caused by the undesirable fluctuation in the light emitted from the light source. The outputs of logarithmic circuits 5, 6 and 7 are connected, respectively, to low pass filters 8, 9 and 10 and also to differential amplifiers 11, 12 and 13. The outputs of low pass filters 8, 9 and 10 are also connected to differential amplifiers 11, 12 and 13, respectively. Each differential amplifier calculates a difference between the outputs from the logarithmic circuit and the low pass filter and amplifies the obtained difference. Therefore, each differential amplifier produces a photoelectric volume pulsating signal obtained at a particular wavelength light. The pulsation in this signal is caused by the volume change of venous blood in the measuring portion and, therefore, the pulsating signal contains information about absorption coefficient of venous blood.

Differential amplifiers 11, 12 and 13 are connected, respectively, to full-wave rectifiers 14, 15 and 16, each of which is defined by a half-wave rectifier and an integrator. In each full-wave rectifier, the output signal from the differential amplifier are full-wave rectified and, thereafter, under the control of CPU 26, the rectified signal is integrated for a given time, such as 0.9 second, and thereafter, it is temporarily held for a period of time. The temporarily held signals from full-wave rectifiers 14, 15 and 16 and a signal from light amount detector 17 are selected by analog multiplexer 18 and are sequentially transmitted to double integrator 19a of A/D converter 20. Which signal multiplexer selects is controlled by CPU26.

Double integrator 19a, comparator 19b and a counter provided in CPU 26 define a double integration type A/D converter. Thus, the signals sequentially applied to double integrator 19a are converted to digital signals. After A/D conversion of each signal, the integrators in full-wave rectifiers 14, 15 and 16 are reset to discharge the integrated signal. Accordingly, each of the integrators in full-wave rectifiers 14, 15 and 16 repeats the operations of integration, hold and discharge in a predetermined frequency, and the A/D conversion is carried out in relation to such operations. Similarly, A/D conversion of output signal from light amount detector 17 is carried out repeatedly with a predetermined frequency. Each of the converted digital signals from full-wave rectifiers 14, 15 and 16 is subtracted by an offset voltage of the corresponding full-wave rectifier, which is previously converted to a digital signal and stored, thereby obtaining three amplitude signals which are in relation to the amplitude of the corresponding pulsating signal. Using the first amplitude signal, which is based on the 805 nanometer wavelength light, and the second amplitude signal, which is based on the 710 nanometer wavelength light, a first SaO$_2$ signal (hereinafter indicated as SaO$_2$(1)) is obtained. Similarly, using the first amplitude signal and the third amplitude signal, which is based on the 650 nanometer wavelength light, a second SaO$_2$ signal (hereinafter indicated as SaO$_2$(2)) is obtained. The obtained SaO$_2$(1) and SaO$_2$(2) are stored for a period of time. As will be described in detail later, SaO$_2$(1) will be used for the detection of any noise signal caused by the undesirable movement of the body member. The obtained SaO$_2$(1) and SaO$_2$(2) are calculated and renewed after every predetermined period of time. As to SaO$_2$(2), the newly obtained SaO$_2$(2) and those obtained in the several previous operations are used for obtaining an average SaO$_2$(2) which will be displayed through display device 25. Detailed steps for obtaining the average SaO$_2$(2) will be described later.

The pulsating signal produced from differential amplifier 11 is applied to wave-shaping circuit 21 in which the pulsating signal is compared with a predetermined threshold level thereby changing the pulsating signal to a binary pulse signal which takes either a HIGH level or LOW level. The binary signal is applied to CPU 26 which detects the step up and step down of the pulse for calculating the pulse repetition rate, thereby calculation the pulse rate of the patient, i.e., the number of heart beats per one minute. Similar to SaO$_2$(1) and SaO$_2$(2), the pulse rate is calculated repeatedly after predetermined periods of time and is displayed through a display device 25. A detail of calculation of pulse rate will be described later.

Ampere meter control 22 changes the pulsating signal obtained from differential amplifier 11 to a signal appropriate for driving an ampere meter 29 which indicates whether or not the pulsating signal is in a normal condition. Recorder control 23 changes the pulsating signal obtained from differential amplifier 11 to a signal appropriate to be applied to a recorder (not shown). Upon depression of a switch provided on display device 25, the information displayed on display device 25 can be immediately transferred to printer 27 for producing a hard copy of data, such as average SaO₂ and pulse rate, for graph recording.

The signals representing the average SaO₂ and pulse rate can be produced in a digital form through output device 28. In the case where the obtained SaO₂ and pulse rate exceeds the upper limit or falls below the lower limit, it is possible that the patient is in a dangerous condition. In such a case, an alarm is required to enable a prompt action to the patient. According to the present invention, it is possible to set the upper and lower limits of each of SaO₂ and pulse rate by operating various switches provided on range setting device 24. The set values are indicated on display device 25.

The alarm may be produced by way of sound from alarm device 30 and/or visual indication on display device 25. An operator can select whether or not to produce the alarm sound by a suitable switch means provided on alarm device 30. Furthermore, it is possible to change the mode of alarm device 30 such that it may be prohibited from generating a sound alarm even when the obtained result exceeds the upper limit and/or falls below the lower limit.

Light amount detector 17 is a circuit which changes the style of the output signal from logarithmic circuit 7 in a fashion applicable for the A/D conversion input signal. The signal produced from the light amount detector 17 is converted to a digital signal after every predetermined period of time, and the converted digital signal is used for determining whether or not the amount of light from light source 1 is at a reasonable level. In the case where the light from light source 1 is very strong, the operation of the photoelectric cells and logarithmic circuits 5, 6 and 7 saturates, thereby deteriorating the accuracy of the calculated result. Also, when the body member is offset the light path between light source 1 and photoelectric cells, the received light amount becomes great, thereby disabling the calculation of SaO₂. A similar problem arises when the light is very weak. In this case, the signals produced from the photoelectric cells and logarithmic circuits 5, 6 and 7 are so poor that it is impossible to carry out the SaO₂ measurement with a reasonable accuracy. Therefore, in order to watch and detect whether or not the received light is at a reasonable level, the output signal from light amount detector 17 is converted to a digital form and is examined whether or not it is within a predetermined range.

Figure 2:
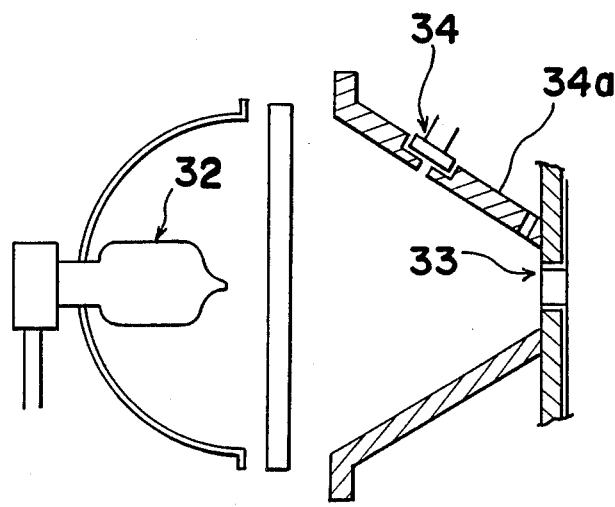

Referring to FIG. 2, the description is directed to the way how the noise signal, caused by the undesirable fluctuation in the light amount, is eliminated. The light from light source 1, such as from a halogen lamp 32, is directed to an end face of optical fiber 33. A reference number designated a photoelectric cell mounted in a hood 34a for monitoring the halogen light. Since photoelectric cell 34 and the end face of optical fiber 33 are positioned adjacent each other, the same type of light and approximately the same amount of light will be directed to both places. Thus, the spectral characteristics will be the same and the amount of light will be proportional between the light received by the cell 34 and by the end face of fiber 33. According to the embodiment shown in FIG. 2, only one photoelectric cell 34 is shown, but it is possible to provide a plurality of such cells. The light directed to the end face of optical fiber 33 is further directed to a measuring portion where the body member should be located. The light which has transmitted through the body member is directed to light receiver 2, at which the light is separated to spectrum for obtaining lights at three different wavelengths. The separated lights are directed to three photoelectric cells 36, 37 and 38.

Referring to FIG. 3, a circuit for receiving signals from photoelectric cells 34, 36, 37 and 38 and for producing signals having no influence of light fluctuation and carrying only the information about the attenuation of light caused only by the body member is shown. Photoelectric cell 34 of monitor circuit 3 is connected to I/V converter 35. Similarly, Photoelectric cells 36, 37 and 38 of light receiver 2 are connected to I/V converters 39, 40 and 41, respectively. Each I/V converter is provided for converting the current signal from the photoelectric cell to a voltage signal. Each of logarithmic amplifiers 42, 43 and 44 has two inputs A and B and calculates a ratio of A to B and logarithmically compresses the obtained ratio. A further detail of the circuit is given below.

The light separated at light receiver 2 and having a particular wavelength, such as 805 nanometers, impinges on photoelectric cell 36. Thus, the spectral characteristics of the light received by photoelectric cell 36 differs from that received by photoelectric cell 34 in the monitor receiver. Accordingly, the degree of change in the light amount, caused by the light intensity change of light source 1, at the photoelectric cell 36 is not the same as that at the photoelectric cell 34. Thus, the noise signals produced by the light intensity change in light source 1 can not be eliminated by merely taking a ratio between outputs from I/V converts 39 and 35 and logarithmically compressing the obtained ratio. In order to eliminate the noise signals produced by the light intensity change in light source 1 by the steps of taking a ratio between outputs from I/V converts 39 and 35 and logarithmically compressing the obtained ratio, it is necessary to match the spectrum distribution of the light directed to photoelectric cell 34 and that to photoelectric cell 36. To this end, one way is to provide a spectral divider, such as a prism, in front of photoelectric cell 34. However, this method requires three spectral dividers for monitoring lights at three different wavelengths. According to the present invention, no spectral divider is provided to photoelectric cell 34, but the signal obtained from cell 34 is electrically processed. There is a certain relationship between a ratio of change in the light amount, caused by the light intensity change of light source 1, to the intensity of light impinging on photoelectric cell 34 and a ratio of change in the light amount, caused by the light intensity change of light source 1, to the intensity of light impinging on photoelectric cell 36. More specifically, there is a certain relationship between a ratio of AC component, caused by the light intensity change of light source 1, to DC component in the output voltage from I/V converter 35 and a ratio of AC component, caused by the light intensity change of light source 1, to DC component in the output voltage from I/V converter 39. According to the present invention, the ratio of AC component, caused by the light intensity change of light source 1, to DC component in the output voltage from I/V converter 35 is so adjusted such that these ratios have the same amount.

The same adjustment as described above is made for each of the two other lights having different wavelengths. These adjustments are accomplished by AC/DC converters 45, 46 and 47 shown in FIG. 3. Thus, a ratio of AC component, caused by the light intensity change of light source 1, to DC component in the output voltages from AC/DC converter 45 is fixed substantially the same as a ratio of AC component, caused by the light intensity change of light source 1, to DC component in the output voltages from I/V converter 39. Similarly, a ratio of AC component, caused by the light intensity change of light source 1, to DC component in the output voltages from AC/DC converter 46 is fixed substantially the same as a ratio of AC component, caused by the light intensity change of light source 1, to DC component in the output voltages from I/V converter 40, and a ratio of AC component, caused by the light intensity change of light source 1, to DC component in the output voltages from AC/DC converter 47 is fixed substantially the same as a ratio of AC component, caused by the light intensity change of light source 1, to DC component in the output voltages from I/V converter 41.

In other words, AC/DC converter 45 produces a signal representing a ratio of AC component to DC component with respect to the light directly measured from light source 1 and having a wavelength of 805 nanometers. Other AC/DC converters 46 and 47 produce similar signals, but they are based on lights having wavelength of 710 nanometers and 650 nanometers.

Accordingly, logarithmic amplifiers 42, 43 and 44 produce signals having no noise signal caused by the light intensity change of light source 1.

Figure 4:
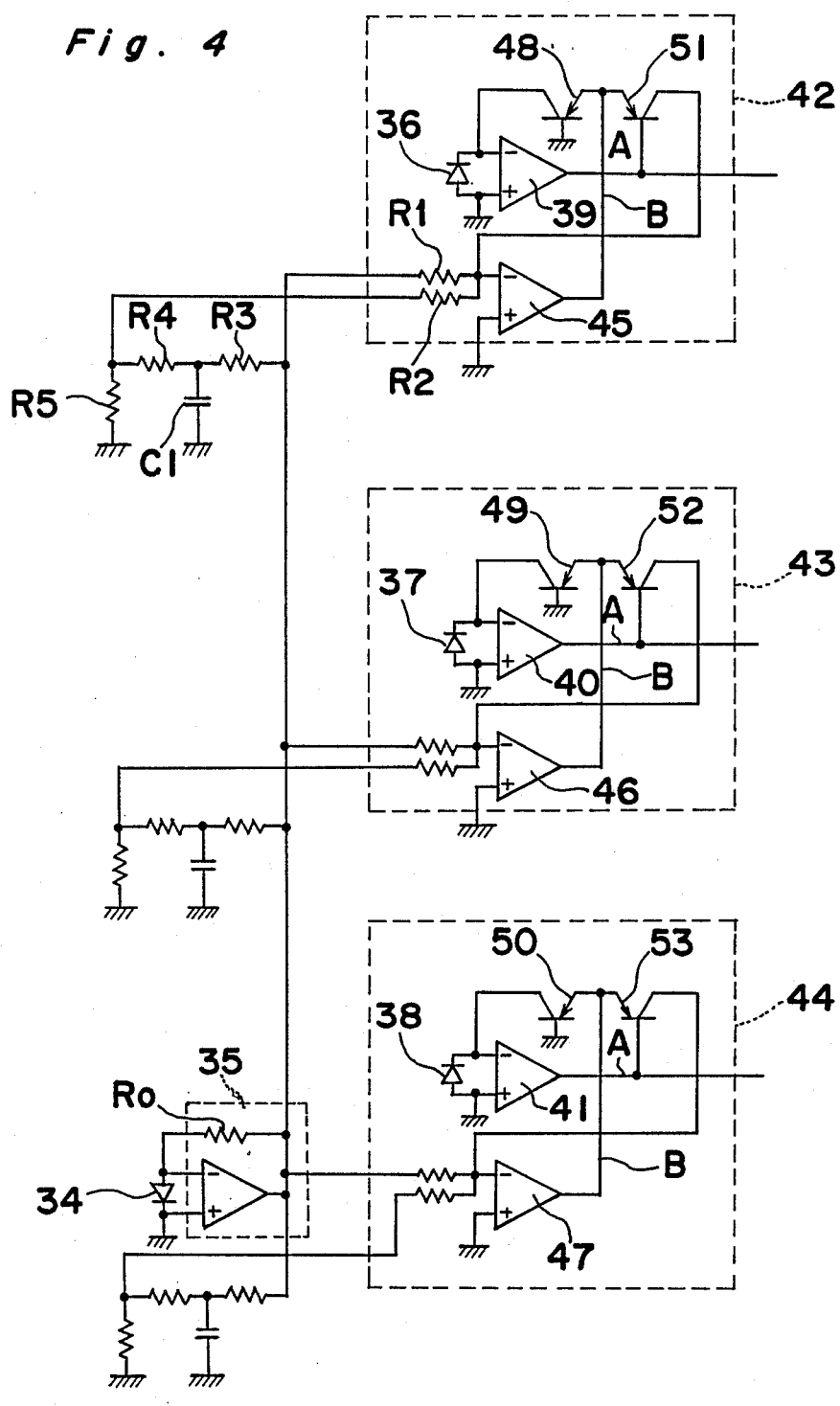
FIG. 4 is a circuit diagram showing a detail of logarithmic amplifiers and the associated parts thereto.

Referring to FIG. 4, a circuit diagram of circuits 39–44 is shown. In the circuit shown in FIG. 4, the output currents from photoelectric cells 36, 37 and 38 are applied directly to a logarithmic compression circuits.

Logarithmic amplifier 42 has a transistor 48 which has its collector connected to the cathode side of photoelectric cell 36. Therefore, the collector current of transistor 48 is substantially the same as photocurrent I1 can be given by a product of a light intensity Iow of light at the wavelength 805 nanometers from light source 1 and the transmittance, or reflectance, of the body member. The light intensity Iow is a composite signal of DC component Iowdc and AC component Iown representing the noise signal caused by the light intensity change of light source 1, and therefore, the following equation may be obtained:

$$Iow = (Iowdc + Iown)F = Iowdc(1+Nw)F,$$

wherein $$Nw = \frac{Iown}{Iowdc}$$

and F is a constant determined by the sensitivity of the photoelectric cell and transmittance of the body member. Since a photocurrent Ir from photoelectric cell 34 is proportional to the light intensity Io of light from light source 1 in every wavelength, and since Io has a DC component and AC component Ion caused by the light intensity change of light source 1, the following equation may be obtained:

$$Ir = K1(Iodc + Ion) = K1 \times Iodc(1+N),$$

wherein $$N = \frac{Ion}{Iodc}$$

and K1 is a constant. The output voltage Vr produced from I/V converter 35, which is coupled to photoelectric cell 34, can be given as follows:

$$Vr = Ro \times K1 \times Iodc(1+N).$$

Thus, a current that flows through a resistor R1 may be written as follows:

$$\frac{Vr}{R1} = K1 \times \frac{R0}{R1} \times Iodc\,(1+N),$$

and through a resistor R2, a current that has no AC component flows, which may be written as follows:

$$Vr \times \frac{R}{R+R3+R4} \times \frac{1 \times K1 \times Iodc}{R2} = \frac{K1 \times R \times Ro}{(R+R3+R4)R2} \times Iodc$$

wherein R is equal to a value of a parallel connection of resistors R2 and R5. Thus, $$R = \frac{R2 \times R5}{R2 + R5}.$$

Accordingly, the collector current of transistor 51 can be written as follows:

$$K1\left[Iodc \times Ro\left(\frac{1}{R1} + \frac{R}{R2(R+R3+R4)}\right) + \frac{1}{R1}N\right] =$$

$$K1 \times Iodc \times Ro\left(\frac{1}{R1} + \frac{R}{R2(R+R3+R4)}\right)\left(1 + N/\left(1 + \frac{R \times R1}{R2(R+R3+R4)}\right)\right).$$

Therefore, logarithmic amplifier 42 produces an output voltage Vout which can be written as:

$$Vout = K2 \times \log_e \frac{F(1+Nw)}{K1Ro\left(\frac{1}{R1} + \frac{R}{R2(R+R3+R4)}\right)\left(1 + N/\left(1 + \frac{R \times R1}{R2(R+R3+R4)}\right)\right)}$$

$$= K2 \log_e \frac{F}{K1Ro\left(\frac{1}{R1} + \frac{R}{R2(R+R3+R4)}\right)} + \log_e \frac{1+Nw}{1 + N/\left(1 + \frac{R \times R1}{R2(R+R3+R4)}\right)}.$$

In the above equation, the first term indicates the information about the measured body member and the second term indicates the information about the noise signal caused by the light intensity change of light source 1. Here, by selecting the resistor values of resistors R1–R5 to fulfill an equation $$N / \left(1 + \frac{R \times R1}{R2(R + R3 + R4)}\right) = N_w,$$

the second term, indicating the noise signal, can be eliminated from the output voltage Vout.

In the case where it is required to make the ratio of AC component, caused by the light intensity change of light source 1, to DC component in the output current from photoelectric cell 34 greater than the ratio of AC component, caused by the light intensity change of light source 1, to DC component in the collector current of transistor 51, it can be done by merely replacing a low pass filter defined by a capacitor C1 with a high pass filter.

Although the above description is directed to a logarithmic amplifier 42, other logarithmic amplifiers 43 and 44 can be arranged in the same way, and therefore, a detailed description therefor is omitted for the sake of brevity.

Figure 5:
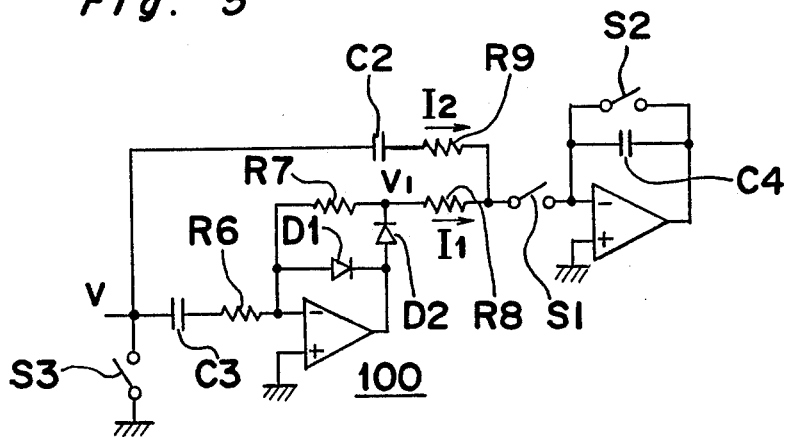
FIG. 5 is a circuit diagram showing an example of a standard full-wave rectifier.
Figure 6:
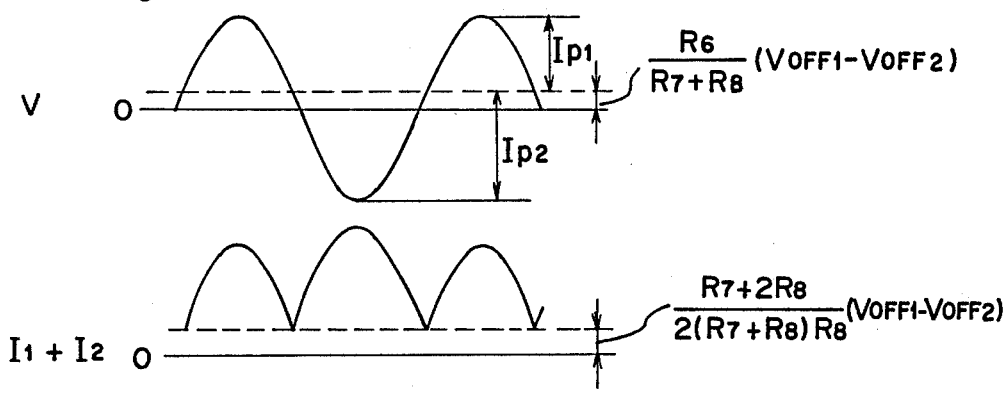
FIG. 6 is a graph showing a pulsating signal and a rectified signal, both carried on unwanted offset voltage.
Figure 7:
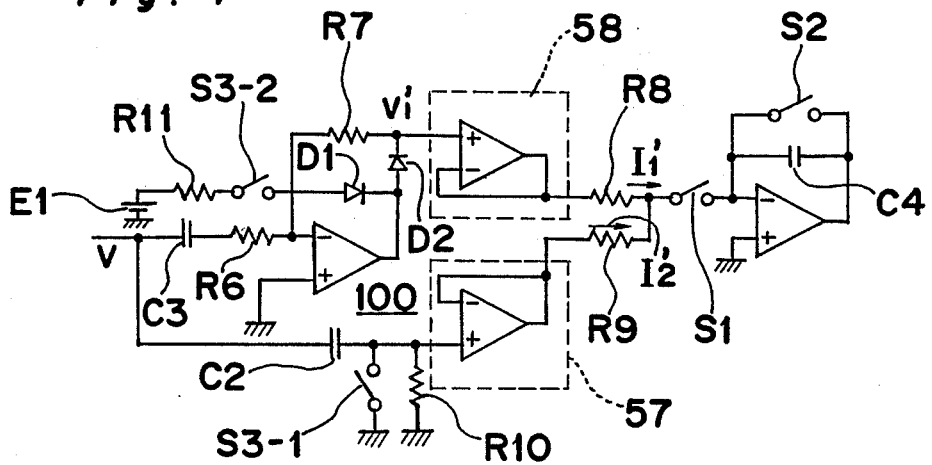
FIG. 7 is a circuit diagram showing an improved full-wave rectifier.

Next, referring to FIGS. 5-7, the description is directed to full-wave rectifiers 14, 15 and 16, each of which is provided for converting the AC signal based on the pulsation of the patient to DC signal. An example of a standard full-wave rectifier is shown in FIG. 5. Since the frequency of pulsation is generally low, the standard full-wave rectifier comprises a half-wave rectifier and an integrator.

When a sine wave signal is applied to the circuit of FIG. 5, an output current I1 of the half-wave rectifier has a greater waveform in the negative side than that in the positive side and, therefore, a peak value Ip1 in the positive side from a reference level and a peak value Ip2 in the negative side are not equal to each other (Ip1≠Ip2). Such an unbalance is caused by a bias current of the half-wave rectifier and integrator flowing through resistor R8 or a current that flows through resistor R8 by the difference in the offset voltages of the half-wave rectifier and integrator. Also, the integrator has two switches S1 and S2 for intergrating the input signal when switch S1 is on and switch S2 is off. Then, when switch S1 turns off, the integration stops and the circuit holds the integrated value for a predetermined time. Thereafter, switch S2 turns on to discharge a capacitor C4 of the integrator. The integrator repeats this operation. Since capacitor C2 and resistor R9 in series connection are connected to the input of the integrator, the current I2 takes a transient change which gives rise to an error in the output signal. Also, in the case when it is required to detect only the offset voltage of the circuit of FIG. 5, switch S3 is turned on to shortcircuit the input and switch S1 is turned on and switch S2 is turned off thereby integrating only the offset voltage. However, the offset voltage obtained while switch S3 is on and the offset voltage obtained while switch S3 is off (that is when the AC signal is applied) do not coincide with each other.

In the case when a sine wave signal V $$V = a \times \sin \phi t$$

is applied to the circuit of FIG. 5, an output voltage V1 of the half-wave rectifier, if R6=R7, can be given as follows:

$$V1 = Voff1 - a \times \sin \phi t$$

when $$V \leq R6 \frac{Voff1 - Voff2}{R7 + R8}$$

and $$V1 = \frac{Voff1 \times R8 + Voff2 \times R7}{R7 + R8}$$

when $$V > R6 \frac{Voff1 - Voff2}{R7 + R8},$$

wherein Voff1 is an offset voltage of the half-wave rectifier and Voff2 is an offset voltage of the integrator. Accordingly, current I1 can be given as follows:

$$I1 = \frac{1}{R8} (Voff1 - a \times \sin \phi t - Voff2)$$

when $$V \leq R6 \frac{Voff1 - Voff2}{R7 + R8}$$

and $$I1 = \frac{Voff1 - Voff2}{R7 + R8}$$

when $$V > R6 \frac{Voff1 - Voff2}{R7 + R8}.$$

Also, when the circuit is in a stable condition after a period of time from the turn on of switch S1, I2 may be written as:

$$I2 = \frac{1}{R9} \times a \times \sin \phi t.$$

In the case when R9=2R8, a current I1+I2 that is applied to capacitor C2 in the integrator may be written as:

$$I1 + I2 = \frac{1}{R8} (Voff1 - Voff2 - \frac{1}{2} a \times \sin \phi t)$$

when $$V \leq R6 \frac{Voff1 - Voff2}{R7 + R8}$$

and $$I1 + I2 = \frac{Voff1 - Voff2}{R7 + R8} + \frac{1}{2R8} a \times \sin \phi t)$$

when $$V > R6 \frac{Voff1 - Voff2}{R7 + R8}.$$

This is shown in graphs of FIG. 6. When the current I1+I2 is integrated by an integrator, the output of the integrator and the amplitude a of the sine wave do not have a linear relationship therebetween. Therefore, even when the applied signal is subtracted by an offset voltage which has been measured and stored before receiving the signal, a correct signal which is proportional to the amplitude of the true signal can not be obtained. This is due to the fact that the current produced by the difference in the offset voltages of the half-wave rectifier and integrator flows through resistor R7. This may be prevented by making the offset voltages equal to each other (Voff1=Voff2), or even when Voff1≠Voff2, by arranging the circuit in such a manner as to prevent any current from flowing through resistor R7. Also, since the integrator repeats the steps of charging, holding and discharging, switch S1 repeats on and off operations at a predetermined time sequence. In this case, a current flowing through capacitor C2 and resistor R9 shows a transient change and, therefore, there will be an error contained in the output signal from the integrator.

Referring to FIG. 7, a full-wave rectifier according to a preferred embodiment is shown, which has eliminated the above-described drawbacks. When compared with the standard full-wave rectifier described above, the full-wave rectifier of FIG. 7 has buffer circuits 57 and 58 connected between half-wave rectifier 100 and integrator. Each buffer circuit is defined by an operational amplifier. By buffer circuit 58, no current will flow through resistor R7 even when there is a difference in the offset voltages. The output voltage V1' of half-wave rectifier 100, obtained when switches S3-1 and S3-2 (FIG. 7) are turned off and AC signal is applied, can be given as follows:

$$V1' = Voff1 - V$$

when $$V \leq 0$$

and $$V1' = Voff1$$

when $$V > 0.$$

Here, R6=R7, and bias currents to buffer circuit 58 and half-wave rectifier 100 are so small that they can be disregarded of. When switch S1 turns on after a sufficient time from the turn on of switch S3-1, an input current I1'+I2' to the integrator can be given as:

$$I1' + I2' = \frac{1}{2R8}(2Voff1 - 3Voff2 + 2Voff3 + Voff4) - \frac{V}{2R8}$$

when $$V \leq 0$$

and $$I1' + I2' = \frac{1}{2R8}(2Voff1 - 3Voff2 + 2Voff3 + Voff4) - \frac{V}{2R8}$$

when $$V > 0.$$

Accordingly, the output from integrator has a linear relationship with the amplitude of input signal to the fullwave rectifier. Therefore, a value proportional to the input signal may be obtained through the steps of measuring and memorizing the offset voltage without receiving the signal, and subtracting the stored signal from the output of the integrator at the time when the signal is applied.

In the case where only the offset voltage is measured, it is necessary not to permit any signal from being applied. During the measuring of SaO2, the offset voltage of full-wave rectifier may be varied. Therefore, it is required to measure the offset voltage once in several minutes. In the case of FIG. 5, the offset voltage may be measured using switch S3 to shortcircuit the input of full-wave rectifier. But in such a case, a transient response takes place immediately after the closure of switch S3 and, therefore, a correct measurement can not be ensured until a stable condition is established. Since it takes a time period before the stable condition is established, it is necessary to wait for a period of time to start again the measuring of SaO2. According to the preferred embodiment shown in FIG. 7, switches S3-1 and S3-2 are provided to shorten the transient period and to obtain the stable condition quickly. When only the offset voltage of the full-wave rectifier is measured, switches S3-1 and S3-2 are turned on to integrate outputs from buffer circuits 57 and 58. The time it takes, from turn on of switch S3-1, to stable the input of buffer circuit 57 is determined by capacitor C2 and the resistance of switch S3-1 during an on state. Since the resistance of switch S3-1 during its on state is very low when compared with the resistance of resistor R10, the time it takes to stabilize the circuit is very short. Also, when switch S3-2 turns on, a current flows from voltage source E1 through resistor R11 and switch S3-2 to diode D11. Since such a current flowing through resistor R11 is selected to be relatively large, the output from the full-wave rectifier will be equal to Voff1. Therefore, it is possible to measure the offset voltage immediately after the turn on of switches S3-1 and S3-2 and, thus, it is possible to shorten the period before the restart of SaO2 measuring.

By the use of the above described circuit for removing the noise signals caused by the light intensity change of light source 1, and the above described full-wave rectifier which provides a correct offset voltage, SaO2 and pulse rate can be measured with a high accuracy even when the received signal has a relatively low level.

Next, the description is directed to the motion artifact detecting method. The motion artifact detecting method, according to the present invention, is possible in either the continuous or periodic motion artifact and, therefore, the influence caused by the change in the patient is very low. According to the present invention, the pulsating change in the blood volume in a detecting portion of the body member is measured using light at three different wavelengths, and the measured results are obtained from three differential amplifiers 11, 12 and 13 shown in FIG. 1a. SaO2 can be obtained using two pulsating signals at two different wavelengths. Since there are three pulsating signals at three different wavelengths, it is possible to obtain SaO2 in three different ways, using two of the three signals. In the case where the motion artifact does not exist, the obtained SaO2s result in the same amount. However, when the motion artifact exists, there will be some differences among the obtained SaO₂ results. According to the present invention, using two of the three signals in two different combinations, two SaO₂s are obtained through two different calculation steps. The obtained two SaO₂s are compared with each other to calculate a difference therebetween. When the difference is greater than a reference level, it is so determined that the motion artifact exists.

Since the difference between SaO₂s differs relative to the amount of SaO₂ even if the degree of motion artifact is the same, the above-mentioned reference level differs dependingly on the obtained SaO₂. This is further described below.

From three differential amplifiers 11, 12 and 13, the pulsating change in the blood volume as measured at light receiving portion 2 with respect to three different wavelengths are obtained. The obtained pulsating signals are applied to full-wave rectifiers 14, 15 and 16 in which they are full-wave rectified and then, are integrated for a predetermined period of time. The integrated results, which are voltage signals, are then held at rectifiers 14, 15 and 16, respectively, and are sequentially converted to digital form and stored. The offset voltages of full-wave rectifiers 14, 15 and 16, which are previously measured and stored, are subtracted, respectively, from the signals held in full-wave rectifiers 14, 15 and 16. The subtracted results, which will be referred to as Y1, Y2 and Y3, are then stored. The results Y1, Y2 and Y3 are in relation to the amplitude of pulsating signals produced from differential amplifiers 11, 12 and 13, respectively.

When the results Y1, Y2 and Y3 are obtained correspondingly to the light at wavelengths 805, 710 and 650 nanometers, respectively, SaO(1) is obtained using Y1 and Y2 by the following equation:

$$SaO_2(1) = A1(Y2/Y1)^2 + B1$$

and SaO(2) is obtained using Y1 and Y3 by the following equation:

$$SaO_2(2) = A2(Y3/Y1)^2 + B2.$$

Figure 12:
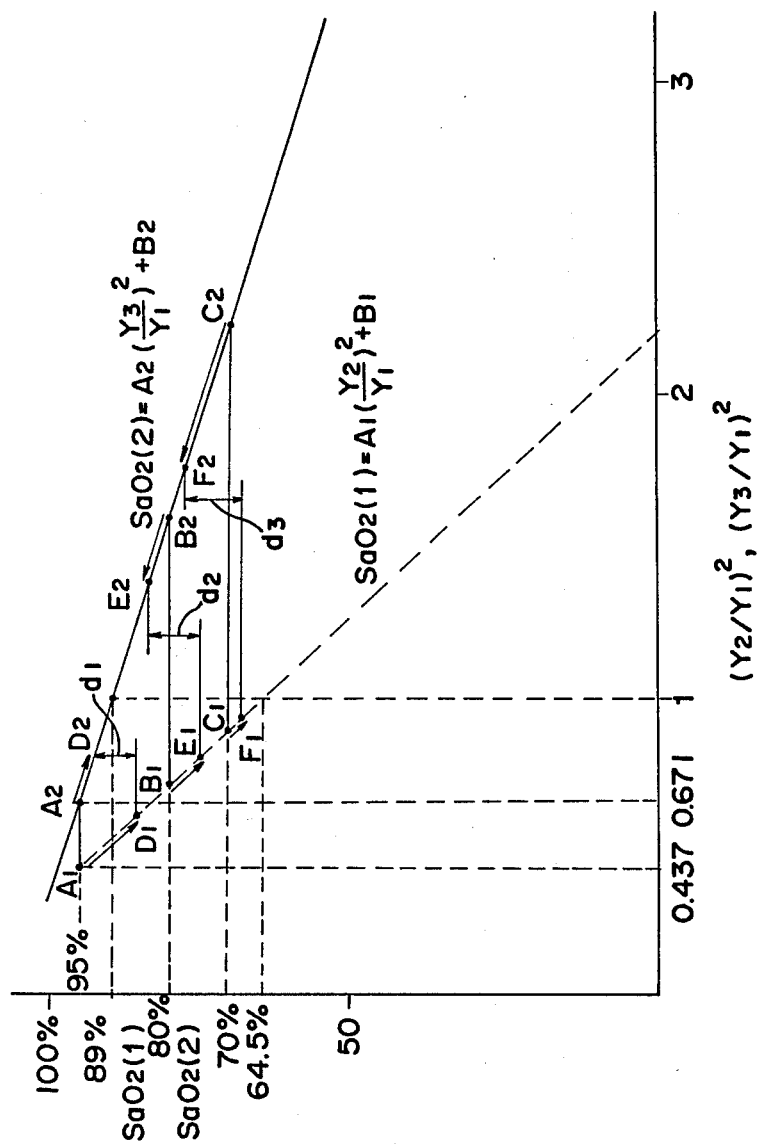
FIG. 12 is a graph showing a relationship between calculated $SaO_2$ and a square of amplitude ratio.

A relationship between SaO₂(1) and $(Y2/Y1)^2$ and a relationship between SaO₂(2) and $(Y3/Y1)^2$ are shown in a graph of FIG. 12, in which abscissa and ordinate represent $(Y2/Y1)^2$ (or $Y3/Y1)^2$) and SaO₂(1) (or SaO₂(1)) in percentage. In the case where there is no motion artifact, SaO₂(1) and SaO₂(2) coincide with each other. However, if the motion artifact exists, $(Y2/Y1)^2$ and $(Y3/Y1)^2$ are both approximately equal to one and, therefore, SaO₂(1) and SaO₂(2) do not coincide with each other. In this case, the noise signal has almost no relationship to the wavelength. For example, suppose that a true SaO₂ is 95%, if there is no motion artifact, the obtained results are:

$$(Y2/Y1)^2 = 0.437$$

and $$(Y3/Y1)^2 = 0.671.$$

However, if there is motion artifact, the same noise signal will be imposed on each of signals Y1, Y2 and Y3 at three wavelengths. Thus, the obtained results are:

$$(Y2/Y1)^2 = 1$$

and $$(Y3/Y1)^2 = 1.$$

In this case, SaO₂(1) and SaO₂(2) approach near 64.5% and 89.7%, respectively. Thus, the difference between SaO₂(1) and SaO₂(2) becomes great. Then, when the absolute value of such a difference:

$$|SaO_2(1) - SaO_2(2)|$$

becomes greater than the reference level, it is detected that the motion artifact is present. Since such a difference $|SaO_2(1) - SaO_2(2)|$ differs, even when the noise signal level caused by the motion artifact is the same, with respect to the true SaO₂, the reference level is made variable. In the case where the motion artifact is present, the true SaO₂ can not be detected directly and, therefore, the reference level is made variable with respect to SaO₂(1) and SaO₂(2). The graph shown in FIG. 12 is obtained when the signals Y1, Y2 and Y3 are pulsating signals obtained correspondingly to the light at wavelengths about 805, 710 and 650 nanometers, respectively. In the case where the motion artifact is not present, and when the true SaO₂ is 95%, 80% or 70%, respectively, A1, B1 and C1 in FIG. 12 indicate points obtained in connection with SaO₂(1) and A2, B2 and C2 indicate points obtained in connection with SaO₂(2). In the case where the motion artifact is the same for the three different SaO₂s, points A1, B1 and C1 are shifted to points D1, E1 and F1, and points A2, B2 and C2 are shifted to points D2, E2 and F2, respectively. In this case, when the motion artifact is present to each true SaO₂, the differences $|SaO_2(1) - SaO_2(2)|$ are indicated by d1, d2 and d3. Such differences change dependingly on the true SaO₂ (or SaO₂(1) or SaO₂(2)). Such a change is depicted in FIG. 8.

Figure 8:
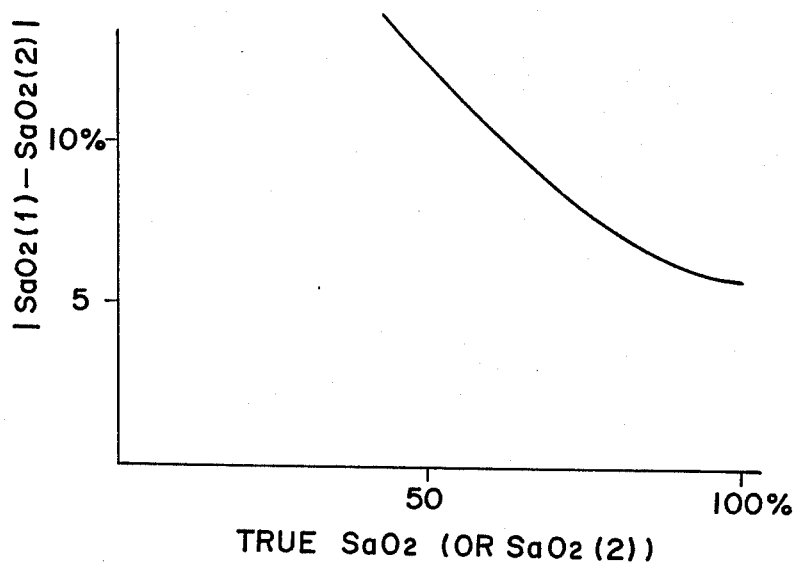
FIG. 8 is a graph showing a relationship between a difference $|SaO_2(1) - SaO_2(2)|$ and true $SaO_2(2)$.

When the motion artifact having a level greater than a predetermined level is detected by a comparison between the difference $|SaO_2(1) - SaO_2(2)|$ and a reference level (f(SaO₂(1), SaO₂(2))), the reference level (f(SaO₂(1), SaO₂(2))) may be approximately the same as that indicated on FIG. 8.

As described above, according to the present invention, the motion artifact detecting method does not take the step of detecting the waveform or amplitude change of the pulsating signal. Thus, the difference in the detected results between patients is very small. Furthermore, the motion artifact that occurs periodically can be detected.

In the case where three or more SaO₂s are obtained using pulsating signals at three or more different wavelengths of light, more than two differences are available between two of the obtained SaO₂s. To detect the motion artifact using the obtained differences, a particular reference level is given to each difference for the comparison between each difference in an absolute value and the corresponding reference level. When at least one difference in the absolute value exceeds the corresponding reference level, it may be so determined that the motion artifact is present. Instead, the determination of presence of the motion artifact may be done when two or more differences in the absolute value exceed the corresponding reference level.

Next, a method for obtaining an average of SaO₂ is described.

According to the oximeter of the present invention, SaO₂(1) and SaO₂(2) are calculated after each predetermined period of time. It is possible to display either $SaO_2(1)$ or $SaO_2(2)$ after each cycle of calculation operation. However, in the case where the accuracy of the calculated $SaO_2(1)$ of $SaO_2(2)$ can not be ensured, such as when the intensity of the light that reaches the light receiving portion is not appropriate or when the amplitude of the pulsating signal is greater or smaller than an appropriate range, each calculated $SaO_2(1)$ or $SaO_2(2)$ may include more or less error and, therefore, it is not preferable to display the calculated $SaO_2(1)$ or $SaO_2(2)$. When the accuracy can not be ensured, the prior art oximeter is so arranged as to skip the indication of the calculated $SaO_2$. If such an error occurs rather frequently, the display is interrupted frequently and the indication may be effected so few that the using of the machine is worthless. For example, if the calculation for $SaO_2(1)$ and $SaO_2(2)$ is carried out once every second, but the display is effected only once every several seconds due to the failure of acquiring accuracy, it is uncomfortable for the operator to watch the display.

In order to solve this problem, the following method has been proposed.

It is very rare for $SaO_2$ to change rapidly, such as within one second. Therefore, if the calculated $SaO_2$ has a poor accuracy at a calculation cycle Ti, the display may continue to indicate the old $SaO_2$ obtained in the previous calculation cycle Ti-1. In this way, there will be no interruption of the display.

However, according to this method, if such a poor condition where the accuracy can not be ensured lasts for a long time, the display continues to indicate the old $SaO_2$ during that time. This is very dangerous because the patient's $SaO_2$ may change during that time, whereas the display remains to indicate the same old data, resulting in a misjudgement.

In consideration of the above, according to the present invention, the display will not be interrupted even when the obtained data has a poor accuracy, but when the poor condition continues, the display will automatically interrupted to avoid any misjudgement by using the old data. To this end, the oximeter according to the present invention has the following improvement. According to the oximeter of the present invention, $SaO_2(1)$ and $SaO_2(2)$ are calculated and stored after ever predetermined period of time. When $SaO_2(2)$ is calculated and stored at the end of a calculation cycle Ti, which is indicated as $SaO_2(2)(Ti)$, a predetermined number of $SaO_2(2)$s including that $SaO_2(2)(Ti)$, such as k+1 $SaO_2(2)$s are examined whether or not each has a required accuracy.

Then it is detected whether or not the number of $SaO_2(2)$s that have passed the examination is greater than the predetermined number M, provided that M is equal to or smaller than k+1. In other words, $SaO_2(2)$s obtained in the previous calculation cycles back to cycle Ti-k are examined to determine whether each of them has a required accuracy. If the number of $SaO_2(2)$s, including $SaO_2(2)(Ti)$, that have passed the examination is equal to or greater than M, M $SaO_2(2)$s of all the passed $SaO_2(2)$s counted from the one obtained most recent, i.e., the one obtained close to the recent cycle Ti are taken out to calculate an arithmetic average among them. The average of M $SaO_2(2)$s selected in the above described manner is displayed.

On the contrary, if the number of $SaO_2(2)$s that have passed the examination is less than M, the indication of $SaO_2$ stops and, instead, a warning will be effected.

Then, at the end of the next calculation cycle Ti+1, $SaO_2(2)$s obtained in the calculation cycles from Ti+1−k to Ti+1 are examined for their accuracy. If there are equal to or more than M $SaO_2(2)$s that have the required accuracy, M $SaO_2(2)$s with the required accuracy are counted from the most recently obtained $SaO_2(2)$, and the their arithmethic average is calculated and displayed. If there are less than M $SaO_2(2)$s with the required accuracy, the display vanishes and a warning is effected. Thereafter, similar operations are carried out repeatedly.

According to the above described method of the present invention, the display will fail to indicate an average $SaO_2(2)$ only if k−M+2 $SaO_2(2)$s with poor accuracy are obtained successively. Therefore, even if the inaccurate $SaO_2(2)$s are obtained intermittently, there will be no interruption in the display.

Furthermore, since the display vanishes when the inaccurate $SaO_2(2)$ are obtained successively in k−M+2 cycles of operations, there will be no fear of displaying the old same $SaO_2(2)$ for a long time.

In the above description, k and M may be such that, if one calculation cycle is one second long, k may be equal to seven and M may be equal to 5. In this case, the display will not vanish unless $SaO_2(2)$s having poor accuracy are obtained in four or more successive calculation cycles. Thus, if inaccurate $SaO_2(2)$s are produced successively for a long time, the display continues to indicate the old average not more than four seconds, but after that the display vanishes and a warning is effected. If inaccurate $SaO_2(2)$s are produced successively for three seconds, the average based on the old $SaO_2(2)$ will be displayed, but after that, a newly obtained average will be displayed. Thus, there will be no interruption in the display.

Next, the description will be directed to the display device and other surrounding devices coupled to the microcomputer. According to the prior art oximeter, the obtained $SaO_2$ is displayed digitally or by a pointer of an ampere meter. Thus, it is possible to obtain an instantaneous value of $SaO_2$, but the way how $SaO_2$ changes with respect to time can not be obtained directly. An improvement has been made wherein an output terminal for producing the obtained $SaO_2$ signal in voltage is provided for connection with a pen-recorder, or a pen-recorder itself is incorporated in the oximeter. However, in the case where the measuring takes place for a long time, much recording paper is necessary for the continuous recording. In this case, if the significant section is only a part of the recorded paper, the remaining part of the paper is worthless, resulting in the waste of the recording paper. Furthermore, in the case where only an instantaneous amount is required, the pen-recorder also operates, again resulting in the waste of the recording paper.

Figure 9:
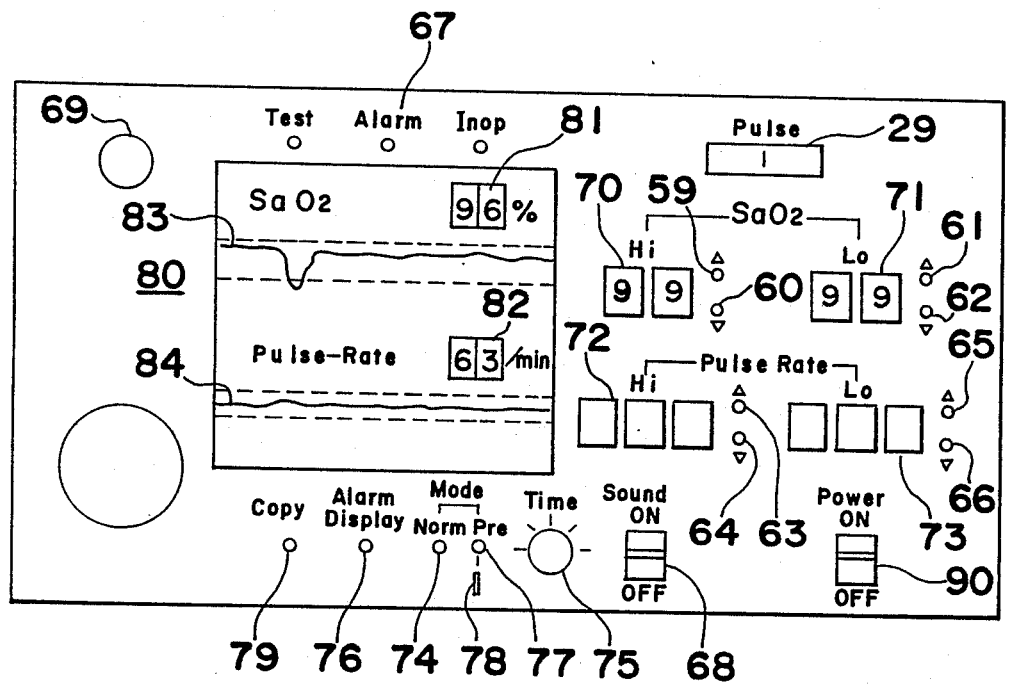
FIG. 9 is a plan view of a control panel.

Referring to FIG. 9, according to the present invention, in order to solve the above problem, a two-dimension display device 80 is employed in a control panel. Accordingly, the average $SaO_2$ and pulse rate are indicated numerically and at the same time, $SaO_2$ and pulse rate are depicted graphically in which abscissa and ordinate representing time and amplitude, respectively.

According to the embodiment shown in FIG. 9, the two-dimension display device 80 is defined by a color CRT in which: the average $SaO_2$ as calculated by CPU 26 is indicated digitally at 81; the detected pulse rate is indicated digitally at 82; the time change of $SaO_2$ is indicated graphically at 83; and the time change of pulse rate is indicated graphically at 82.

On the right-hand side of the CRT, control panel further includes a range setting device which corresponds to device 24 shown in FIG. 1a. The range setting device has buttons 59–66 and display sections 70–73. Display sections 70 and 71 are provided for numerically indicating upper and lower limits of SaO$_2$, and display sections 72 and 73 are provided for numerically indicating upper and lower limits of pulse rate. When button 59 is depressed, the upper limit of the SaO$_2$ as indicated at section 70 gradually increases, and when button 60 is depressed, it gradually decreases. When button 61 is depressed, the lower limit of the SaO$_2$ as indicated at section 71 gradually increases, and when button 62 is depressed, it gradually decreases. Similarly, when button 63 is depressed, the upper limit of the pulse rate as indicated at section 72 gradually increases, and when button 64 is depressed, it gradually decreases. When button 65 is depressed, the lower limit of the pulse rate as indicated at section 73 gradually increases, and when button 66 is depressed, it gradually decreases.

Normally, a button 74 is held in the depressed position, setting a normal mode, so that newly obtained data, such as SaO$_2$ and pulse rate will be indicated at sections 81 and 82 on the CRT, and at the same time, such data will be plotted at the left-hand ends of graphs 83 and 84. Accordingly, as the time passes, graphs 83 and 84 shift in the right-hand direction, when viewed in FIG. 9. Furthermore, on the CRT, the upper and lower limits of SaO$_2$ and pulse rate as set and indicated at sections 70–73 are also given by dotted lines. The degree of time scale of the graphs on the CRT can be changed by a rotary switch 75. Thus, the graphs depicted on the CRT may cover the past half hour change, one hour change, five hours change, or any other time span depending on the set position of rotary switch 75.

A button 76 is provided for effecting the alarm display on the CRT. When button 76 is depressed, the alarm is displayed through the CRT in such a manner as to distinguish the display between the case when the newly obtained SaO$_2$ or pulse rate is within the set range and the case when it falls out of the set range. More specifically, when the newly obtained SaO$_2$ or pulse rate is within the set range determined by the upper and lower limits, the graph is plotted, e.g., in green light, but if the newly obtained SaO$_2$ or pulse rate exceeds above the upper limit, the graph is plotted, e.g., in red, and below the lower limit, it is plotted, e.g., in blue. Furthermore, a similar color change may be effected to the digital displays at 81 and 82.

A button 77 and a lever 78 are provided for setting a preview mode for reproducing any desired previous data on the CRT. A button 79 is provided for obtaining a hard copy. When button 79 is depressed, the data displayed on CRT is printed on a sheet of paper. It is to be noted that digital data of SaO$_2$ and pulse rate displayed at sections 81 and 82 on the CRT may be omitted when making a hard copy. Also, such digital data may be produced after every predetermined period of time.

Next, the description will be directed to a flow chart shown in FIGS. 10–11. According to the operation described hereinbelow as an example case, one calculation cycle for calculating SaO$_2$(1), SaO$_2$(2) and pulse rate and processing the calculated results takes one second. When a power switch 90 is turned on, an indication, such as "CAL" is displayed on the CRT for indicating that the system is now establishing an initial condition. Then, by manipulating buttons 59–66, the upper and lower limits for the SaO$_2$ and/or pulse rate can be varied to desired amounts while viewing the numbers at display sections 70–73 representing such limits change gradually. For example, when button 59 is depressed and held in the depressed position, a counter (not shown) provided in CPU 26 increases at a predetermined rate and, accordingly, the number at section 70, representing the upper limit of SaO$_2$, increases at the rate of "1". On the contrary, when button 60 is held depressed, the number at section 70 decreases at the same rate. Other buttons 60–66 operate in a similar manner. When any of these buttons 60–66 is operated, an operation indicated by a flow chart of FIG. 11 takes place.

Figure 10A:
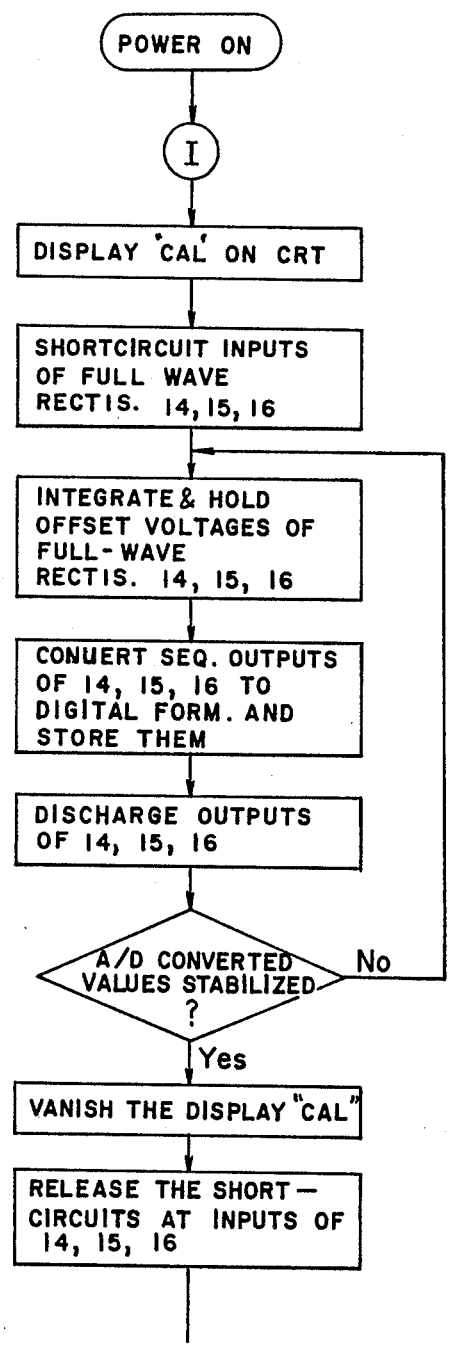
FIGS. 10a–10e taken together as shown in FIG. 10 show a flow chart for the control operation of calculation carried out in the oximeter of the first embodiment.
Figure 10B:
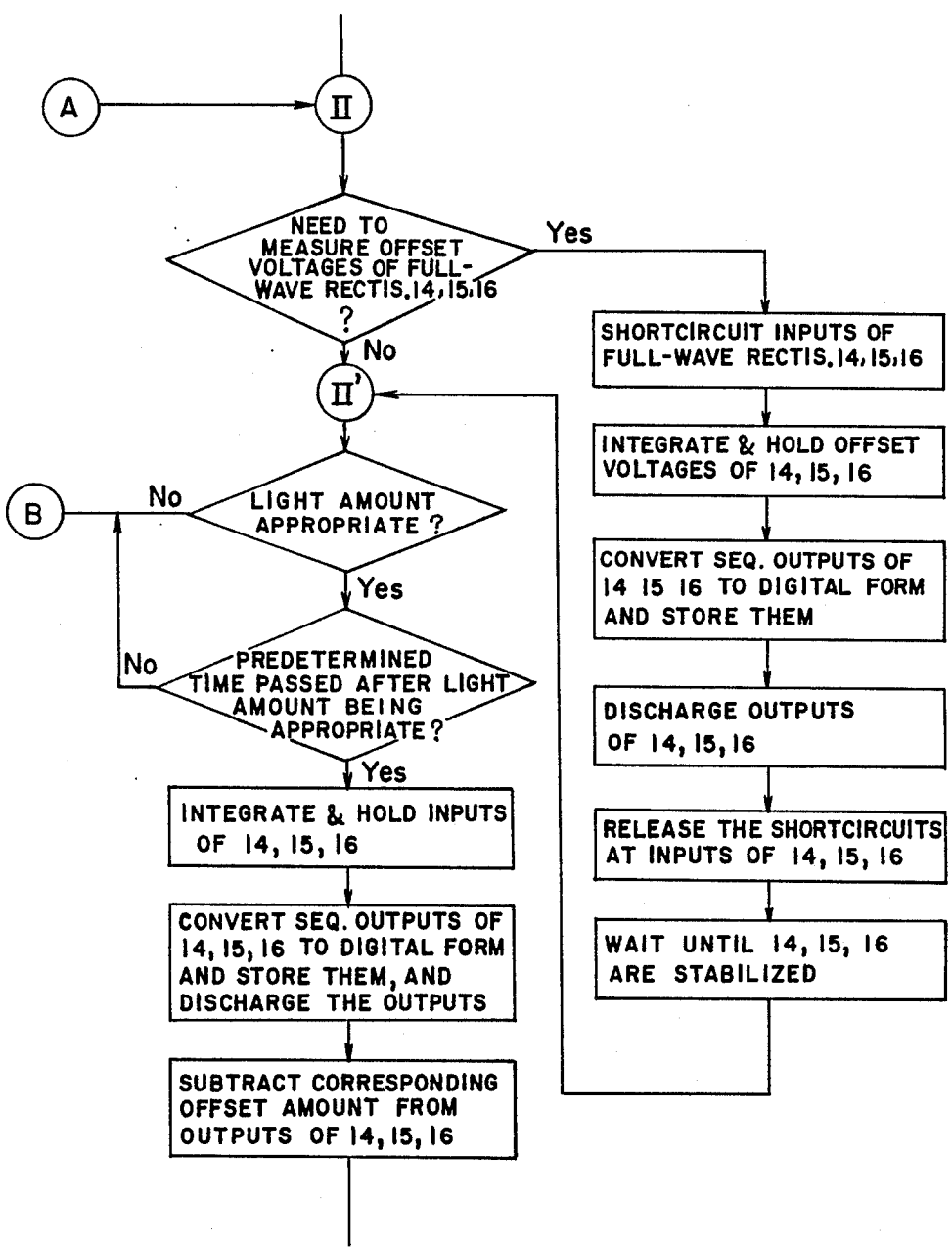

Then, CPU 26 controls various switches in fullwave rectifiers 14, 15 and 16 to produce an offset voltage from each rectifier. More specifically, in each full-wave rectifier, as shown in FIG. 7, integration switch S1, switch S3-1 and switch S3-2 are turned on and discharge switch S2 is turned off. Thus, the full-wave rectification is carried out, and the rectified signal is integrated for a predetermined period of time and stored. The stored offset voltage for each full-wave rectifier is converted sequentially to digital form in A/D converter 20, and is stored in a memory (not shown) in CPU 26. The A/D conversion in converter 20 is carried out by double integrator 19a, comparator 19b and counter (not shown) provided in CPU 26. The sequential supply of analog signal to A/D converter 20 is done by multiplexer 18. Then, the discharge switch is controlled by CPU 26 through a switch control line, each capacitor for effecting the integration is discharged. Thus, the steps for obtaining offset voltage data can be summarized as: holding the integrated value of the offset voltage; A/D conversion of the held voltage; memorize; and discharge the integration capacitor in each full-wave rectifier, which are carried out sequentially as indicated in FIG. 10a. Then, using the A/D converted values, it is detected whether or not the circuits are stabilized. More specifically, newly obtained offset voltages from full-wave rectifiers 14, 15 and 16 as stored in CPU in digital form are compared with those obtained in the previous cycle. When the difference therebetween as to each full-wave rectifier is less than a predetermined level, it is so determined that full-wave rectifiers 14, 15 and 16 are all in a stable condition. As indicated in FIG. 10a, when it is detected that any of the full-wave rectifiers is not in the stable condition, the program repeats the above described steps to obtain the offset voltage data. When it is determined that rectifiers 14, 15 and 16 are stabilized, the offset voltage data obtained immediately before such a determination are stored and used for correcting the signals obtained from rectifiers 14, 15 and 16 thereafter. The correction is done by subtracting the offset voltage data from each newly obtained signal. Then, indication "CAL" disappears, ready to carry out the operation of a flow chart starting from step II shown in FIG. 10b.

In the flow chart after step II, it is first detected whether it is necessary to measure the offset voltages of full-wave rectifiers 14, 15 and 16 again, or not. When the detected result is YES, as happens when the offset voltage of any one of the full-wave rectifiers 14, 15 and 16 changes due to some reason, the program is carried out to obtain new offset voltage data which comprises the steps of: setting full-wave rectifiers 14, 15 and 16 in a condition for applying an offset input signal; integrate only the offset voltage obtained in each rectifier; hold the integrated value; convert the integrated values for rectifiers 14, 15 and 16 to digital form in A/D converter 20, sequentially; and store the obtained data of offset voltage for each rectifier in CPU 26. According to one example case, the measuring of the offset voltage is carried out once every several minutes. Thereafter, the program goes to step II'. If it is not necessary to measure the offset voltage, the program directly goes to step II'.

In the flow chart after step II', a signal from light amount detector 17 is transmitted through multiplexer 18 and A/D converter 20 to CPU 26 so as to detect whether the intensity of the light received by light receiver 2 is within an appropriate range which will not adversely affect measuring accuracy.

The output from light amount detector 17 is in relationship to the intensity of light impinging on photoelectric cell 38 in light receiver 2. The A/D converted data of output signal from light amount detector 17 is examined whether or not it is above a first predetermined level and whether or not it is below a second predetermined level. In the case where the light amount is not appropriate, i.e., when the light amount data is not within the range determined by the first and second predetermined levels, the program goes to step III shown in FIG. 10d. If it is within the range, a time it took to change the output of light amount detector 17 to shift from a level above the second predetermined level to a level between the first and second predetermined levels is measured. If the detected time is less than a predetermined time, it is so assumed that the pulsating signal is not stabilized and, therefore, the program goes to step III. A procedure after step III will be described later. If the detected time is greater than the predetermined time, it is so assumed that the pulsating signal is stable. In this case, the program proceeds to receive and process the pulsating signal as described below.

The pulsating signals applied to each of the full-wave rectifiers 14, 15 and 16 are full-wave rectified and integrated for a predetermined period of time. The integrated amounts are held temporarily in the respective rectifiers and are sequentially transmitted, one at a time, through multiplexer 18 for being converted to digital form in A/D converter 20 and stored in CPU 26. The stored pulsating signal data from three rectifiers are, respectively, subtracted by previously stored offset voltage data of three rectifiers. The obtained data after the subtraction, which will be referred to as data Y1, Y2 and Y3, represent amplitudes of pulsating signals applied to rectifiers 14, 15 and 16, respectively.

Figure 10C:
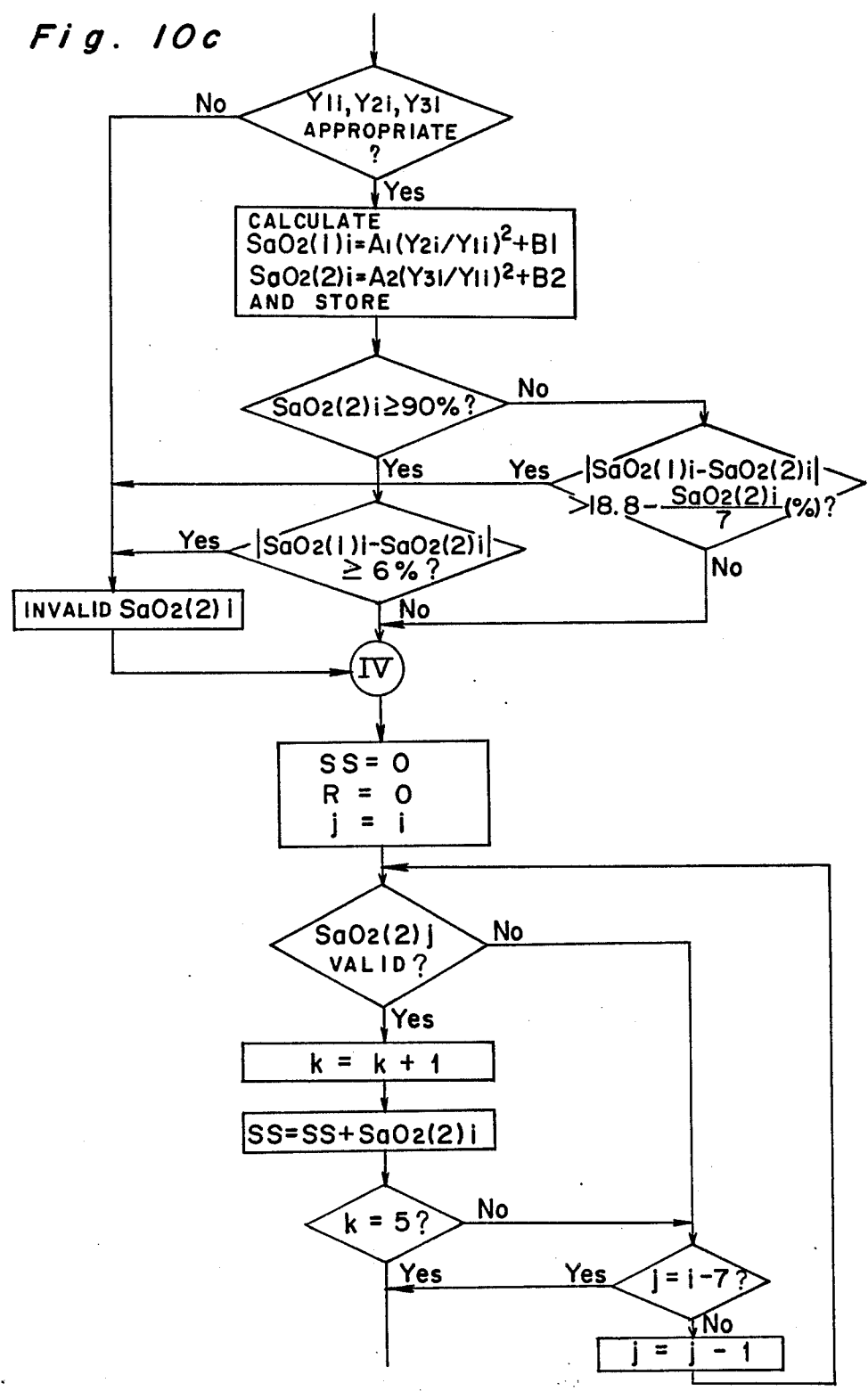

As shown in FIG. 10c, each of data Y1, Y2 and Y3 is examined whether or not it falls within a predetermined range. In other words, it is examined whether each data Y1, Y2 or Y3 is above a third predetermined level and at the same time below a fourth predetermined level. If at least one of data Y1, Y2 and Y3 should fall outside the range between third and fourth predetermined levels, it is assumed that such a data is obtained under a poor condition such as during the circuit saturation or when some noise signals are carried in the circuit and, therefore, such a data lacks accuracy, and is not appropriate. Thus, it is not worth continuing the calculation. In this case, the program invalids $SaO_2(2)i$ and, thereafter, it goes to step IV. On the contrary, when all data Y1, Y2 and Y3 are between third and fourth predetermined levels, it is assumed that the data Y1, Y2 and Y3 have sufficient accuracy and are considered to be appropriate. In such a case, the program advances to carry out the following calculations.

In the following description the data Y1, Y2 and Y3 and $SaO_2(1)$ and $SaO_2(2)$ used and obtained in a cycle Ti of the calculation operation are designated as $Y1i$, $Y2i$ and $Y3i$, $SaO_2(1)i$ and $SaO_2(2)i$, respectively. Thus, in a cycle Ti, by using data $Y1i$, $Y2i$ and $Y3i$, $SaO_2(1)i$ and $SaO_2(2)i$ are obtained through the following calculations:

$$SaO_2(1)i = A1(Y2i/Y1i)^2 + B1$$

and PS $$SaO_2(2)i = A2(Y3i/Y1i)^2 + B2.$$

Thereafter, a comparison between a difference between $SaO_2(1)i$ and $SaO_2(2)i$ in an absolute value and a reference value $f(SaO_2(1)i, SaO_2(2)i)$ are taken. An exemplification under the conditions that:

$$f(SaO_2(1)i, SaO_2(2)i) = 6(\%);$$

and $$SaO_2(2)i \geq 90(\%),$$

or conditions that:

$$f(SaO_2(1)i, SaO_2(2)i) = 18.8(\%) - \frac{SaO_2(2)i}{7} (\%);$$

and $$SaO_2(2)i < 90(\%)$$

will be described.

In the case when $SaO_2(2)i$ is greater than 90%, it is detected that the motion artifact is present when $|SaO_2(1)i - SaO_2(2)i|$ is greater than 6%. And, in the case when $SaO_2(2)i$ is less than 90%, it is detected that the motion artifact is present when $|SaO_2(1)i - SaO_2(2)i|$ is greater than $$18.8(\%) - \frac{SaO_2(2)i}{7} (\%).$$

When it is detected that the motion artifact is present, $SaO_2(2)i$ obtained in the cycle Ti is assumed to have a poor accuracy. In this case, it is memorized that $SaO_2(2)i$ is invalid. Then, the program goes to step IV. If it is detected that the motion artifact is not present, the program goes to step IV with $SaO_2(2)i$ being considered as valid.

A procedure after step IV, which is for calculating an average $SaO_2(2)$, will be described hereinbelow.

From the most recently obtained $SaO_2(2)$, eight $SaO_2(2)$s in the past eight cycles Ti, Ti-1, Ti-2 ... and Ti-7 are sequentially examined whether each $SaO_2(2)$ is valid or not. Therefore, $SaO_2(2)i$, $SaO_2(2)i$-1, $SaO_2(2)i$-2, $SaO_2(2)i$-3, $SaO_2(2)i$-4, $SaO_2(2)i$-5, $SaO_2(2)i$-6, and $SaO_2(2)i$-7 will be examined in the listed order. When the examined $SaO_2(2)$ is valid, it is added to the contents of register SS in CPU 26 and the sum is stored again in register SS. But, if examined $SaO_2(2)$ is invalid, it is disregarded and not added to the contents of register SS. Each time the addition takes place, the contents of register k is incremented by "1". When register k reaches "5", that is when five $SaO_2(2)$s are added, the contents of register SS is divided by five, thereby obtaining an average $SaO_2(2)$. In the case where there is no invalid $SaO_2(2)$ in any one of $SaO_2(2)$i through $SaO_2(2)$i-4, the average will be obtained using these five $SaO_2(2)$s. If there is one invalid $SaO_2(2)$ i contained in these $SaO_2(2)$i through $SaO_2(2)$i-4, and if $SaO_2(2)$i-5 is valid, the average will be obtained after examining $SaO_2(2)$i-5 using five valid $SaO_2(2)$s. If there are less than five valid $SaO_2(2)$ within eight $SaO_2(2)$i through $SaO_2(2)$i-7, the program jumps to step III' (FIG. 10d) after examining $SaO_2(2)$i-7.

If the average $SaO_2(2)$ is obtained, it is stored in a memory and will be used for the display. After obtaining the average $SaO_2(2)$, the pulse rate is calculated in the following manner.

The pulse rate is calculated upon detection of the pulse interval of the pulses produced from wave-shaping circuit 21. The pulse interval may be detecting using either the positive edge or negative edge of the pulses in CPU 26 such that the time is recorded when the positive edge or negative edge of each pulse appears. To calculate the pulse rate, a time interval between the positive edge or negative edge of the newest pulse and that of a pulse counted back eight is detected. Using this time interval, a number of pulses produced in one minute is calculated. When the pulse rate is calculated, it is stored in a memory and will be used for the display.

Then, the calculated average $SaO_2(2)$ is compared with the upper and lower limits of $SaO_2$ as set and indicated at 70 and 71.

In the case where the average $SaO_2(2)$ is between the upper and lower limits, each of high and low alarm memories for $SaO_2$ is stored with "0" and, thereafter, the program goes to step V. However, if the average $SaO_2(2)$ is above the upper limit, the high alarm memory for $SaO_2$ is stored with "1" and, if it is lower than the lower limit, the low alarm memory for $SaO_2$ is stored with "1". Thereafter, the program goes to step V.

In the procedure after step V, the calculated pulse rate is compared with the upper and lower limits as set and indicated at 72 and 73.

In the case where the calculated pulse rate is between the upper and lower limits, each of high and low alarm memories for pulse rate is stored with "0" and, thereafter, the program goes to step VI. However, if the calculated pulse rate is above the upper limit, the high alarm memory for pulse rate is stored with "1" and, if it is lower than the lower limit, the low alarm memory for pulse rate is stored with "1". Thereafter, the program goes to step VI.

In the procedure after step VI, indication of various data on the CRT, and reproduction of the indicated data on a hard copy are effected. First, it is detected whether the mode is either normal mode or preview mode by the detection of conditions of buttons 74 and 77. If button 74 is depressed, the normal mode is selected, and if button 77 is depressed, the preview mode is selected.

Under the normal mode, of the contents of the $SaO_2$ display memory and the pulse rate display memory, the newest $SaO_2$ and pulse rate are displayed at sections 81 and 82, and are plotted on the graphs 83 and 84, respectively, at the most left end thereof. As the new points are plotted at the left-hand end, the lines of the graphs 83 and 84 shift rightwardly. The time scale for the graph is set by switch 75. When button 76 is turned on, the upper and lower limits for the $SaO_2$ as stored in $SaO_2$ high alarm memory display memory and $SaO_2$ low alarm memory display memory are displayed on graph 83 by parallel dotted lines, and, at the same time, the upper and lower limits for the pulse rate as stored in pulse rate high alarm memory display memory and pulse rate low alarm memory display memory are displayed on graph 84 by parallel dotted lines. Also, when button 76 is depressed, the contents of alarm memory for each $SaO_2$ and pulse rate is detected each time the new data is obtained, that is in each cycle. If the $SaO_2$ high alarm memory contains "1", a dot on graph 83 for $SaO_2$ is plotted in red, and if $SaO_2$ low alarm memory contains "1", a dot is plotted in blue. If both alarm memories contain "0", a dot is plotted in green. The same control is done for plotting dots on graph 84 for pulse rate.

When button 76 is not depressed, the above mentioned three color display will not be effected. In this case, graphs 83 and 84 will be indicated only in green.

Also, when the newly obtained $SaO_2$ or pulse rate do not fall within the desired range, "Alarm" LED blinks and, if switch 68 is on, an alarm sound is produced.

Furthermore, when no calculated $SaO_2$ is obtained due to lack of accuracy in the obtained signal, "Inop" LED blinks, and display sections 81 and 82 are made blank and no dots will be plotted and, if switch 68 is on, an alarm sound is produced.

Under the preview mode as established when button 77 is depressed, data obtained in the previous cycle of operation can be viewed through the CRT. Under this mode, when lever 78 is tilted leftwardly, when viewed in FIG. 9, graphs 83 and 84 scan leftwardly and when it is held back in the central position, the scan stops and a still image is displayed. At this position, the left end of each graph represents data obtained in the previous measuring cycle, and at the same time, such previous data at the left end of the graph is numerically indicated at sections 81 and 82. When lever 78 is tilted rightwardly, graphs 83 and 84 scan rightwardly to display more recent data. Even under the previous mode, button 76 and switch 75 function in the same way as in the normal mode. While displaying some previous data on the CRT with lever 78 being held at the central position, one may obtain a hard copy of the displayed image upon depression of button 79 through a copying machine (not shown). Thereafter, the program returns to step II (FIG. 10b) to repeat the same operation.

It is to be noted that operation under the preview mode can be carried out during the integration carried out in full-wave rectifiers 14, 15 and 16 in the program after step II or during the waiting time taken after step III. Therefore, even in the preview mode, new $SaO_2$ and pulse rate are calculated and stored without any interruption.

In the case where A/D converted value of output signal from light amount detector 17 is out of a range determined between a first and second predetermined levels or when the same is shifted from a level above the second predetermined level into said range but it has not passed more than a predetermined time period after such a shift, the program goes to step III. And, in the case where $SaO_2(2)$ is detected as invalid in four subsequent cycles, the program goes to step III'.

Figure 10D:
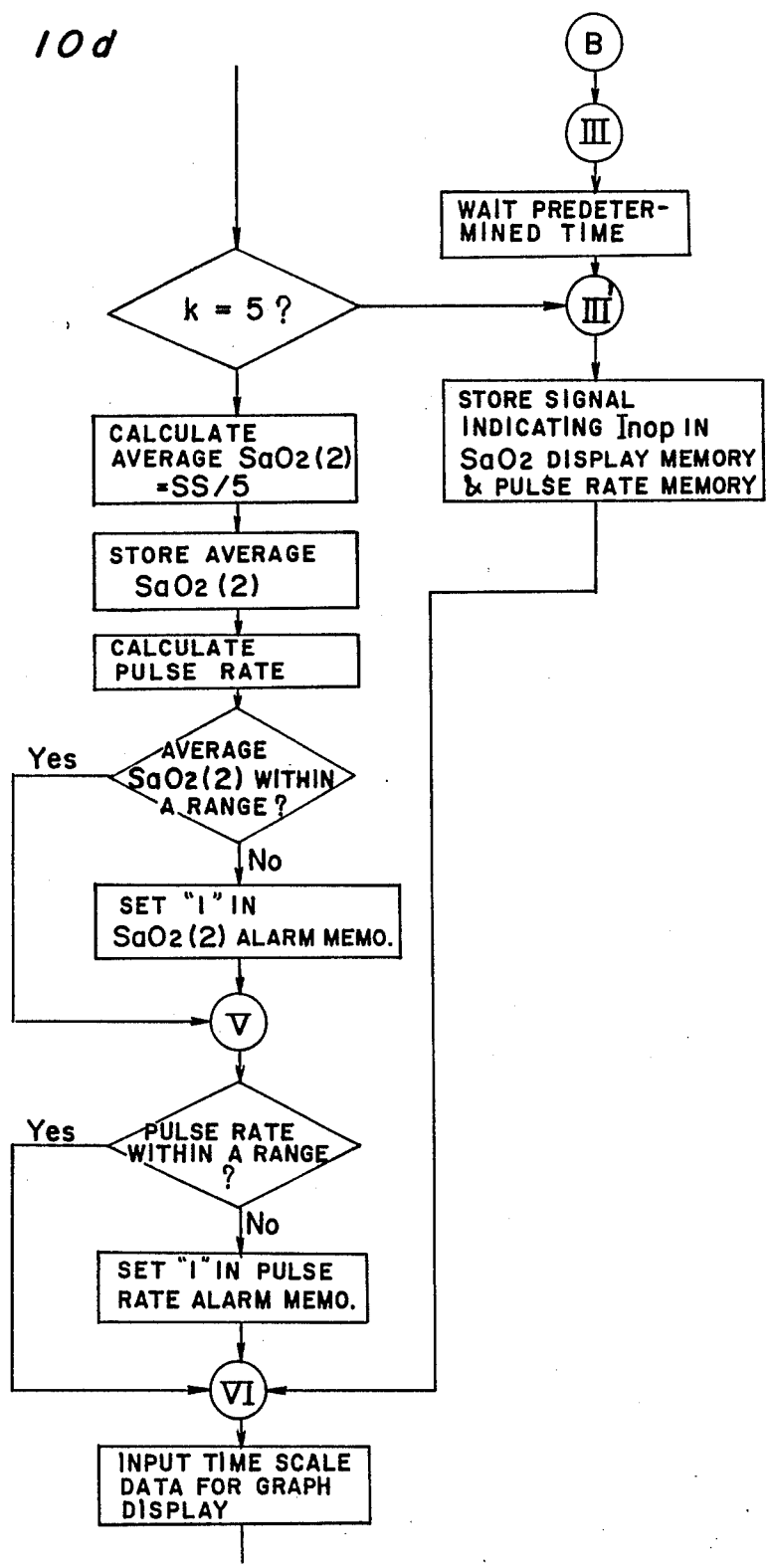
Figure 10E:
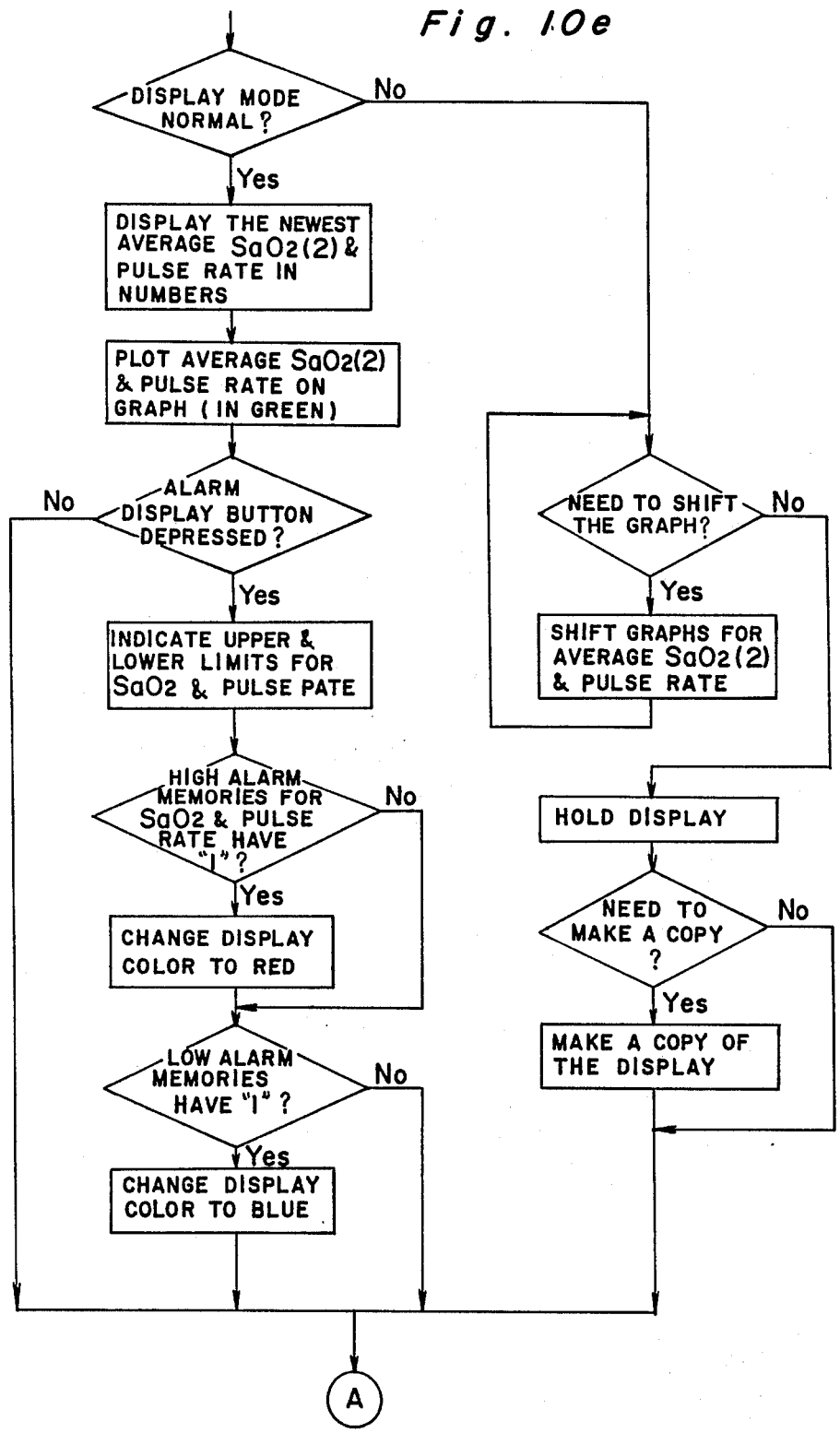

In step III shown in FIG. 10d, a predetermined period of time, which is approximately equal to the integration time (about one second) in full-wave rectifiers 14–16, is counted to withhold the procedure, thereby equalizing the cycle length for both SaO₂ calculation and pulse rate calculation. In step III', a signal representing "Inop" is stored in each of SaO₂ display memory and pulse rate display memory for the indication that the operation is still continuing. Thereafter, the program goes to step VI.

Figure 13:
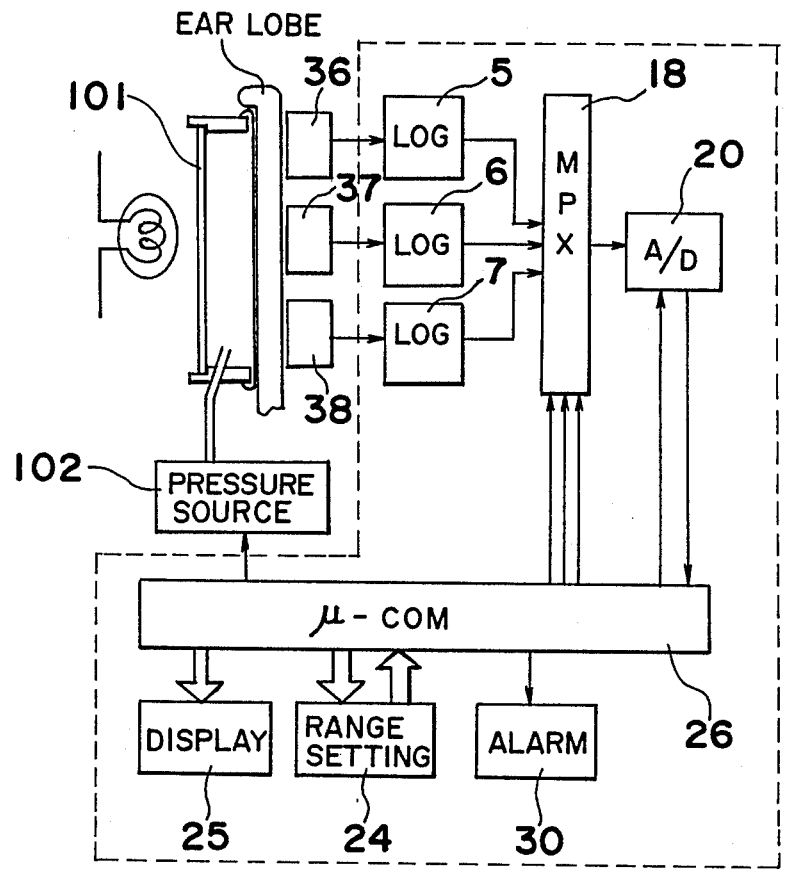
FIG. 13 is a block diagram of an oximeter according to a second embodiment of the present invention.

Referring to FIG. 13, an oximeter according to another embodiment of the present invention is shown. According to the previous embodiment, SaO₂(1) and SaO₂(2) are measured using three pulsating signals at three different wavelengths of light. According to the embodiment shown in FIG. 13, however, SaO₂(1) and SaO₂(2) are measured using three signals at three different wavelengths obtained under bloodless condition and blood filled condition. To this end, the body member, such as an ear lobe is held between pressure applying device 101 and three photoelectric cells 36, 37 and 38. Pressure applying device 101 has a pressure source 102 which is controlled by CPU 26. The outputs of three photoelectric cells 36, 37 and 38 are connected to logarithmic circuits 5, 6 and 7 for the logarithmic compression. The outputs of logarithmic circuits 5, 6 and 7 are connected to multiplexer 18 and further to A/D converter 20 in the same manner as the above embodiment. The operation of the oximeter according to this embodiment will be described below. A detailed description on the calculation for obtaining SaO₂ using signals obtained under bloodless condition and blood filled condition is given in Journal of Laboratory & Clinical Medicine; vol. 34, 1949; pp. 387-401 entitled "Photoelectric Determination of Arterial Oxygen Saturation in Man" by Wood et al. This article, however, teaches the use of two signals for obtaining only one SaO₂ data. In contrast to this, the present invention teaches the use of three signals for obtaining two SaO₂ data.

Figure 14:
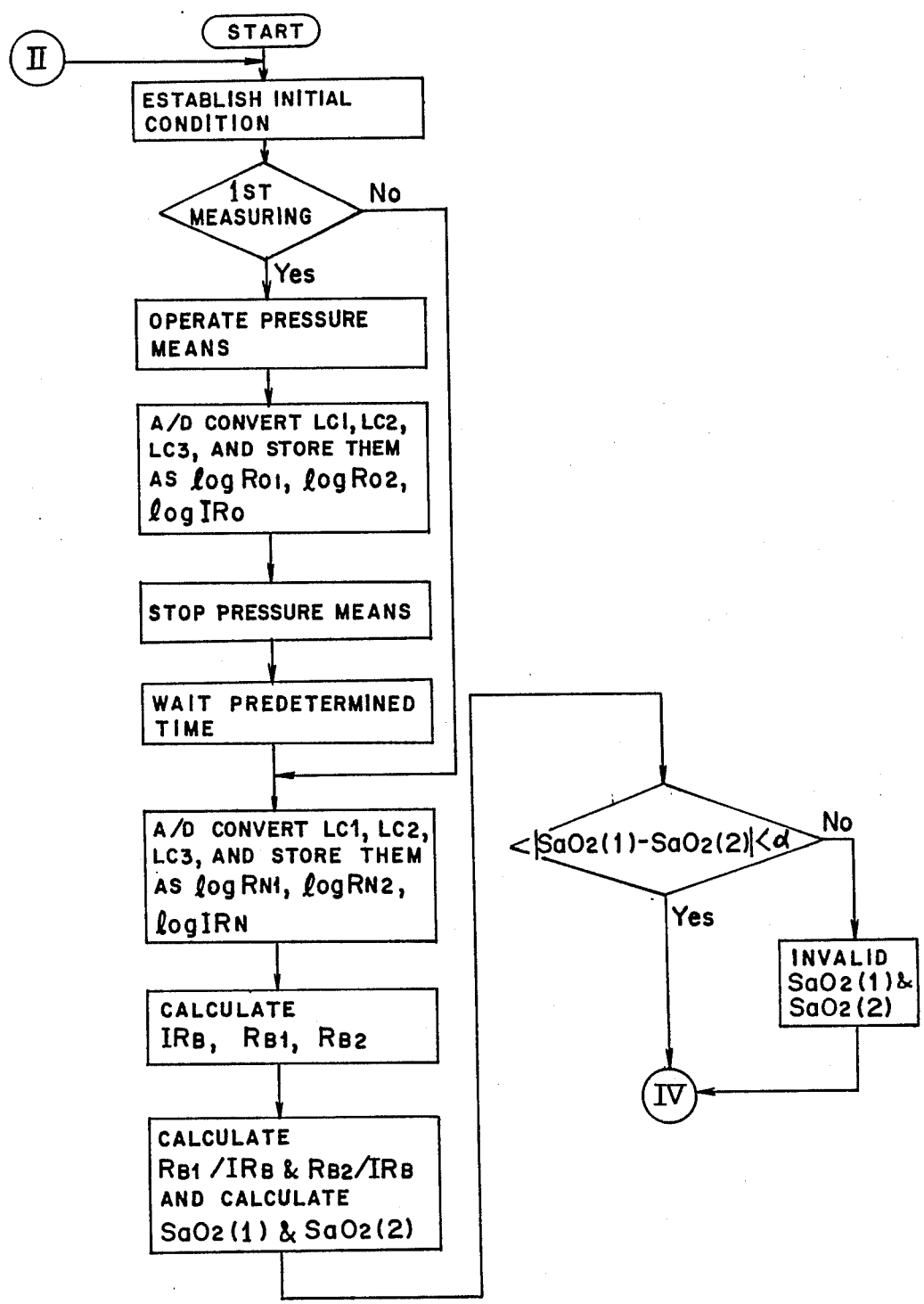
FIG. 14 is a flow chart for the control operation of calculation carried out in the oximeter of FIG. 13.

Referring to FIG. 14, a procedure between steps II and IV for this embodiment is shown. Thus, the procedure up to step II and the procedure after step IV is substantially the same as those shown in FIG. 10a-10e, except that the procedure for this embodiment does not have any steps involved for calculating a pulse rate. After step II, initial condition is established, and thereafter, it is detected whether it is a first cycle or not. If YES, pressure applying device 101 is so operated as to provide a predetermined pressure to the body member, i.e., ear lobe, thereby establishing a bloodless condition. Then, by projecting light to the bloodless ear lobe, signals LC1, LC2 and LC3 produced from logarithmic circuits 5, 6 and 7 are sequentially A/D converted and are stored in CPU 26 as data logRo1, LogRo2 and logIRo. Then, pressure is released and a predetermined period of time is waited so that the ear lobe may be filled with blood. Then, again, by projecting light to the ear lobe, signals LC1, LC2 and LC3 produced from logarithmic circuits 5, 6 and 7 are sequentially A/D converted and are stored in CPU 26 as data logRN1, logRN2 and logIRN. Using these data:

$$IRB = \log IRo - \log IRN = \log \frac{IRo}{IRN}$$

$$RB1 = \log Ro1 - \log RN1 = \log \frac{Ro1}{RN1}$$

and $$RB2 = \log Ro2 - \log RN2 = \log \frac{Ro2}{RN2}$$

are calculated. Then, $$\frac{RB1}{IRB} \text{ and } \frac{RB2}{IRB}$$

are calculated to obtain two data, SaO₂(1) and SaO₂(2). Thereafter, a difference between SaO₂(1) and SaO₂(2) in an absolute value is detected whether it is less than a predetermined amount or not. If the difference is smaller than the predetermined value, it is so considered that the obtained two data, SaO₂(1) and SaO₂(2) have a sufficient accuracy, any will be used as valid data in the procedure after step IV. However, if the difference is greater than the predetermined value, it is so considered that the obtained data SaO₂(1) and SaO₂(2) are poor and have less accuracy. In this case, data SaO₂(1) and SaO₂(2) are considered as invalid. Then, the procedure goes to step IV.

As has been fully described above, according to the oximeter of the present invention, since at least three signals at three different wavelengths are obtained in response to one liquid measuring operation, a reliability of the signal can be detected. For example, signals having noises such as caused by the fluctuation of voltage from the electric power or by the undesirable movement of the body member can be detected, thereby positively eliminating any signal that has an error caused by the motion artifact. Thus, signals having a high reliability can be selected and used for the further procedure, such as calculating an average SaO₂ or displaying the calculated SaO₂.

Furthermore, according to the present invention, the monitoring for monitoring the light in three different wavelengths can be done using only one light photoelectric cell.

Although the present invention has been fully described with reference to several preferred embodiments, many modifications and variations thereof will now be apparent to those skilled in the art, and the scope of the present invention is therefore to be limited not by the details of the preferred embodiments described above, but only by the terms of the appended claims.

What is claimed is:

1. An oximeter for measuring oxygen saturation in arterial blood comprising:
    light source means for projecting light to a body member to be measured;
    light responsive means for receiving the light which has transmitted through said body member and for generating at least first, second and third signals at three different wavelengths;
    calculating means for calculating at least first oxygen saturation data using first and second signals and second oxygen saturation data using first and third signals;
    determining means for determining whether or not a difference between said first and second oxygen saturation data is within a predetermined level; and
    means for designating said first and/or second oxygen saturation data as valid when said difference is within said predetermined level, and as invalid when said difference is not within said predetermined level.

2. An oximeter as claimed in claim 1, wherein said first, second and third signals are pulsating signals which correspond to a heart beat.

3. An oximeter as claimed in claim 1, wherein each of said first, second and third signals include information of a body member in a bloodless condition and also in a blood filled condition.

4. An oximeter as claimed in claim 1, further comprising means for controlling said light source means, light responsive means, calculating means, determining means and designating means to operate in a programmed manner to complete one cycle, and for controlling the same to repeat the cycle.

5. An oximeter as claimed in claim 4, further comprising display means for displaying said valid oxygen saturation data.

6. An oximeter as claimed in claim 5, wherein said display means is a CRT.

7. An oximeter as claimed in claim 5, wherein said display means displays said valid oxygen saturation data in a graph having an axis of time and axis of oxygen saturation data.

8. An oximeter as claimed in claim 5, wherein said display means displays said valid oxygen saturation data in a digital number.

9. An oximeter as claimed in claim 4, further comprising means for obtaining an average oxygen saturation.

10. An oximeter as claimed in claim 9, wherein said average oxygen saturation obtaining means comprises:
    detecting means for detecting the valid oxygen saturation data obtained in the recent predetermined number of cycles;
    means for counting the number of valid oxygen saturation data detected by said detecting means;
    and an averaging means for calculating an arithmetic average of a predetermined number valid oxygen saturation data of those detected by said detecting means when said number counted by said counting means is greater than a predetermined number.

11. An oximeter as claimed in claim 1, further comprising means for setting upper and lower limits for said valid oxygen saturation data, and warning means for producing a warning when said valid oxygen saturation data does not fall in a range between said upper and lower limits.

12. An oximeter for measuring oxygen saturation in arterial blood comprising:
    light source means for projecting light to a body member to be measured;
    light responsive means for receiving the light which has transmitted through said body member and for generating at least first, second and third signals at three different wavelengths;
    detecting means for detecting whether or not an amplitude level of each of said first, second and third signals is within a predetermined range between upper and lower levels;
    selecting means for selecting first, second and third signals which have been detected by said detecting means;
    calculating means for calculating at least first oxygen saturation data using selected first and second signals and second oxygen saturation data using selected first and third signals;
    determining means for determining whether or not a difference between said first and second oxygen saturation data is within a predetermined level; and
    means for designating said first and/or second oxygen saturation data as valid when said difference is within said predetermined level, and as invalid when said difference is not within said predetermined level.

* * * * *